United States Patent
King, Jr.

(10) Patent No.: US 8,481,526 B2
(45) Date of Patent: Jul. 9, 2013

(54) FLUOROQUINOLONE CARBOXYLIC ACID MOLECULAR CRYSTALS

(75) Inventor: Harry M. King, Jr., Webster, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 303 days.

(21) Appl. No.: 12/723,047

(22) Filed: Mar. 12, 2010

(65) Prior Publication Data

US 2010/0311731 A1    Dec. 9, 2010

Related U.S. Application Data

(60) Provisional application No. 61/163,223, filed on Mar. 25, 2009.

(51) Int. Cl.
*A61P 31/04* (2006.01)
*A61K 31/55* (2006.01)
*C07D 401/10* (2006.01)

(52) U.S. Cl.
USPC ..................... 514/217.07; 540/597

(58) Field of Classification Search
USPC .......................... 514/217.04, 217.07; 540/597
See application file for complete search history.

(56) References Cited

U.S. PATENT DOCUMENTS

| 5,447,926 A | 9/1995 | Konno et al. |
| 2002/0182255 A1 | 12/2002 | Roy et al. |

FOREIGN PATENT DOCUMENTS

| JP | 1986225181 | 10/1986 |
| JP | 1989090183 | 4/1989 |
| JP | 2003/300882 A | 10/2003 |
| WO | WO 2010/051291 A1 | 5/2010 |

OTHER PUBLICATIONS

Bernstein, "Analytical techniques for polymorphs, Section 4.3 Thermal methods," Polymorphism in Molecular Crystals, 2002, (p. 104-107).
Byrn et al., "Pharmaceutical solids: A strategic approach to regulatory considerations," Pharma Res, 1995, (vol. 12), (Issue. 7), (p. 945-954).
Byrn et al., "Drugs as molecular solids," Solid-State Chemistry of Drugs, 1999, 2nd ed., (p. 82-85).
Caira, "Crystalline polymorphism of organic compounds," Topics in Current Chem, 1998, (vol. 198), (p. 164-208).
Martindale, Nonionic Surfactants, The complete drug reference, 2005, pp. 1411-1416, 34th ed., Pharmaceutical Press, Great Britain.
Tyle, Iontophoretic Devices for Drug Delivery, Pharmaceutical Research, 1986, pp. 318-326, vol. 3, No. 6, Plenum Publishing Corporation.
Remington, Chapter 20: Interfacial Phenomena, The Science and Practice of Pharmacy, 2006, p. 291.
Remington, Chapter 22: Coarse Dispersions, The Science and Practice of Pharmacy, 2006, pp. 319-337.

*Primary Examiner* — Brenda Coleman
(74) *Attorney, Agent, or Firm* — Toan P. Vo

(57) ABSTRACT

Disclosed herein is a molecular crystal form of the compound (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid. The molecular crystal is characterized by at least one of: (a) an X-ray powder diffraction ("XRPD") spectrum that comprises peaks at 2θ angles of 10.6, 15, 19.7, 21.1, and 22°±0.2°; (b) a DSC melting peak at 288° C.; (c) a $^{13}$C NMR spectrum having peaks at 23.3, 27.7, 41.1, 54.5, 116.6, and 153.5 ppm; and (d) pKa values of 5.65 and 9.91. The compound belongs to the class of fluoroquinolones and is useful as an antibacterial agent.

8 Claims, 34 Drawing Sheets

FIG.7A

| # | 2-THETA | d(A) | BG | HEIGHT | H% | AREA | A% | FWHM |
|---|---|---|---|---|---|---|---|---|
| 1 | 8.800 | 10.0410 | 234 | 1686 | 60.2 | 20751 | 32.1 | 0.209 |
| 2 | 10.776 | 8.2030 | 257 | 333 | 11.9 | 3750 | 5.8 | 0.191 |
| 3 | 12.340 | 7.1671 | 269 | 1365 | 48.7 | 16362 | 25.3 | 0.204 |
| 4 | 16.298 | 5.4342 | 283 | 403 | 14.4 | 5095 | 7.9 | 0.215 |
| 5 | 16.741 | 5.2914 | 301 | 818 | 29.2 | 9971 | 15.4 | 0.207 |
| 6 | 17.562 | 5.0460 | 324 | 295 | 10.5 | 3601 | 5.6 | 0.208 |
| 7 | 17.997 | 4.9249 | 336 | 1080 | 38.5 | 12608 | 19.5 | 0.199 |
| 8 | 18.619 | 4.7618 | 319 | 414 | 14.8 | 6300 | 9.8 | 0.259 |
| 9 | 18.900 | 4.6915 | 304 | 261 | 9.3 | 2940 | 4.6 | 0.191 |
| 10 | 19.762 | 4.4889 | 290 | 881 | 31.4 | 13435 | 20.8 | 0.259 |
| 11 | 20.099 | 4.4143 | 372 | 1099 | 39.2 | 16086 | 24.9 | 0.249 |
| 12 | 20.520 | 4.3247 | 431 | 1021 | 36.4 | 13584 | 21.0 | 0.226 |
| 13 | 21.101 | 4.2068 | 425 | 206 | 7.4 | 2368 | 3.7 | 0.195 |
| 14 | 21.402 | 4.1484 | 385 | 858 | 30.6 | 24655 | 38.2 | 0.488 |
| 15 | 21.780 | 4.0773 | 341 | 2186 | 78.0 | 29908 | 46.3 | 0.233 |
| 16 | 22.821 | 3.8936 | 331 | 232 | 8.3 | 4749 | 7.4 | 0.347 |
| 17 | 23.341 | 3.8081 | 365 | 1702 | 60.7 | 25655 | 39.7 | 0.256 |
| 18 | 24.341 | 3.6538 | 408 | 2786 | 99.4 | 34944 | 54.1 | 0.213 |
| 19 | 24.818 | 3.5847 | 420 | 785 | 28.0 | 9307 | 14.4 | 0.202 |
| 20 | 25.340 | 3.5119 | 435 | 486 | 17.3 | 7422 | 11.5 | 0.260 |
| 21 | 25.479 | 3.4932 | 439 | 267 | 9.5 | 6036 | 9.4 | 0.385 |
| 22 | 25.673 | 3.4671 | 445 | 164 | 5.9 | 5263 | 8.2 | 0.544 |
| 23 | 26.160 | 3.4037 | 531 | 689 | 24.6 | 8764 | 13.6 | 0.216 |
| 24 | 26.619 | 3.3460 | 403 | 2802 | 100.0 | 64559 | 100.0 | 0.392 |
| 25 | 26.880 | 3.3142 | 386 | 1340 | 47.8 | 46992 | 72.8 | 0.596 |
| 26 | 27.138 | 3.2832 | 322 | 490 | 17.5 | 5540 | 8.6 | 0.192 |
| 27 | 28.499 | 3.1294 | 336 | 406 | 14.5 | 5296 | 8.2 | 0.222 |
| 28 | 29.580 | 3.0175 | 402 | 1704 | 60.8 | 26159 | 40.5 | 0.261 |
| 29 | 30.298 | 2.9476 | 418 | 268 | 9.5 | 7007 | 10.9 | 0.445 |
| 30 | 30.578 | 2.9212 | 408 | 461 | 16.5 | 13180 | 20.4 | 0.486 |
| 31 | 30.821 | 2.8988 | 403 | 416 | 14.8 | 9102 | 14.1 | 0.372 |
| 32 | 32.050 | 2.7904 | 356 | 91 | 3.3 | 2133 | 3.3 | 0.397 |
| 33 | 32.242 | 2.7742 | 350 | 135 | 4.8 | 2133 | 3.3 | 0.269 |
| 34 | 32.298 | 2.7694 | 348 | 111 | 4.0 | 2133 | 3.3 | 0.327 |
| 35 | 33.761 | 2.6527 | 371 | 522 | 18.6 | 15010 | 23.2 | 0.489 |
| 36 | 34.179 | 2.6213 | 363 | 697 | 24.9 | 22229 | 34.4 | 0.542 |
| 37 | 34.441 | 2.6019 | 395 | 300 | 10.7 | 11003 | 17.0 | 0.624 |
| 38 | 35.280 | 2.5419 | 394 | 494 | 17.6 | 12679 | 19.6 | 0.436 |
| 39 | 35.721 | 2.5116 | 398 | 236 | 8.4 | 11273 | 17.5 | 0.813 |
| 40 | 37.360 | 2.4050 | 417 | 433 | 15.4 | 9222 | 14.3 | 0.362 |
| 41 | 37.616 | 2.3893 | 418 | 238 | 8.5 | 9552 | 14.8 | 0.683 |
| 42 | 38.377 | 2.3436 | 438 | 379 | 13.5 | 6913 | 10.7 | 0.310 |
| 43 | 38.577 | 2.3319 | 446 | 162 | 5.8 | 4514 | 7.0 | 0.475 |
| 44 | 39.420 | 2.2840 | 451 | 468 | 16.7 | 6963 | 10.8 | 0.253 |

FIG.8A

| # | 2-THETA | d(A) | BG | HEIGHT | H% | AREA | A% | FWHM |
|---|---|---|---|---|---|---|---|---|
| 1 | 10.381 | 8.5150 | 324 | 860 | 23.1 | 28405 | 39.2 | 0.562 |
| 2 | 10.599 | 8.3396 | 382 | 1012 | 27.2 | 25112 | 34.7 | 0.422 |
| 3 | 12.240 | 7.2251 | 328 | 868 | 23.3 | 15045 | 20.8 | 0.295 |
| 4 | 13.800 | 6.4120 | 349 | 571 | 15.4 | 8534 | 11.8 | 0.254 |
| 5 | 14.468 | 6.1174 | 379 | 107 | 2.9 | 3229 | 4.5 | 0.511 |
| 6 | 14.599 | 6.0625 | 379 | 212 | 5.7 | 5272 | 7.3 | 0.422 |
| 7 | 15.020 | 5.8938 | 398 | 946 | 25.4 | 20549 | 28.4 | 0.369 |
| 8 | 15.901 | 5.5692 | 395 | 535 | 14.4 | 7771 | 10.7 | 0.247 |
| 9 | 16.663 | 5.3162 | 359 | 188 | 5.1 | 4052 | 5.6 | 0.366 |
| 10 | 16.817 | 5.2676 | 355 | 297 | 8.0 | 4052 | 5.6 | 0.232 |
| 11 | 17.561 | 5.0461 | 356 | 303 | 8.2 | 14995 | 20.7 | 0.841 |
| 12 | 17.998 | 4.9245 | 358 | 458 | 12.3 | 12748 | 17.6 | 0.473 |
| 13 | 19.098 | 4.6435 | 486 | 235 | 6.3 | 2578 | 3.6 | 0.186 |
| 14 | 19.837 | 4.4720 | 711 | 589 | 15.8 | 9638 | 13.3 | 0.278 |
| 15 | 21.120 | 4.2031 | 790 | 3720 | 100.0 | 72461 | 100.0 | 0.331 |
| 16 | 22.060 | 4.0262 | 666 | 2339 | 62.9 | 46686 | 64.4 | 0.339 |
| 17 | 23.200 | 3.8308 | 541 | 251 | 6.8 | 3371 | 4.7 | 0.228 |
| 18 | 23.963 | 3.7105 | 680 | 368 | 9.9 | 5636 | 7.8 | 0.260 |
| 19 | 24.021 | 3.7017 | 697 | 390 | 10.5 | 5636 | 7.8 | 0.246 |
| 20 | 24.757 | 3.5933 | 873 | 274 | 7.4 | 3836 | 5.3 | 0.238 |
| 21 | 25.281 | 3.5201 | 707 | 485 | 13.1 | 25797 | 35.6 | 0.903 |
| 22 | 25.601 | 3.4768 | 448 | 1124 | 30.2 | 49110 | 67.8 | 0.743 |
| 23 | 25.960 | 3.4294 | 448 | 1003 | 27.0 | 39628 | 54.7 | 0.672 |
| 24 | 27.518 | 3.2387 | 525 | 509 | 13.7 | 8234 | 11.4 | 0.275 |
| 25 | 28.024 | 3.1814 | 541 | 117 | 3.1 | 4326 | 6.0 | 0.631 |
| 26 | 28.240 | 3.1576 | 553 | 191 | 5.1 | 3143 | 4.3 | 0.280 |
| 27 | 28.359 | 3.1446 | 554 | 140 | 3.8 | 3143 | 4.3 | 0.381 |
| 28 | 29.601 | 3.0154 | 536 | 805 | 21.6 | 23626 | 32.6 | 0.499 |
| 29 | 29.998 | 2.9764 | 550 | 237 | 6.4 | 4443 | 6.1 | 0.319 |
| 30 | 31.801 | 2.8116 | 535 | 819 | 22.0 | 24171 | 33.4 | 0.502 |
| 31 | 32.420 | 2.7593 | 599 | 287 | 7.7 | 6632 | 9.2 | 0.393 |
| 32 | 33.988 | 2.6355 | 605 | 100 | 2.7 | 3829 | 5.3 | 0.651 |
| 33 | 34.221 | 2.6181 | 617 | 176 | 4.7 | 3829 | 5.3 | 0.370 |
| 34 | 34.335 | 2.6097 | 628 | 116 | 3.1 | 3029 | 4.2 | 0.445 |
| 35 | 34.826 | 2.5741 | 606 | 132 | 3.6 | 5080 | 7.0 | 0.653 |
| 36 | 35.020 | 2.5602 | 584 | 297 | 8.0 | 6468 | 8.9 | 0.370 |
| 37 | 35.100 | 2.5546 | 575 | 290 | 7.8 | 6468 | 8.9 | 0.379 |
| 38 | 37.295 | 2.4091 | 488 | 95 | 2.6 | 3263 | 4.5 | 0.581 |
| 39 | 39.702 | 2.2684 | 681 | 385 | 10.4 | 6379 | 8.8 | 0.281 |

FIG.20A HCL SALT

FIG.20B FREE FORM

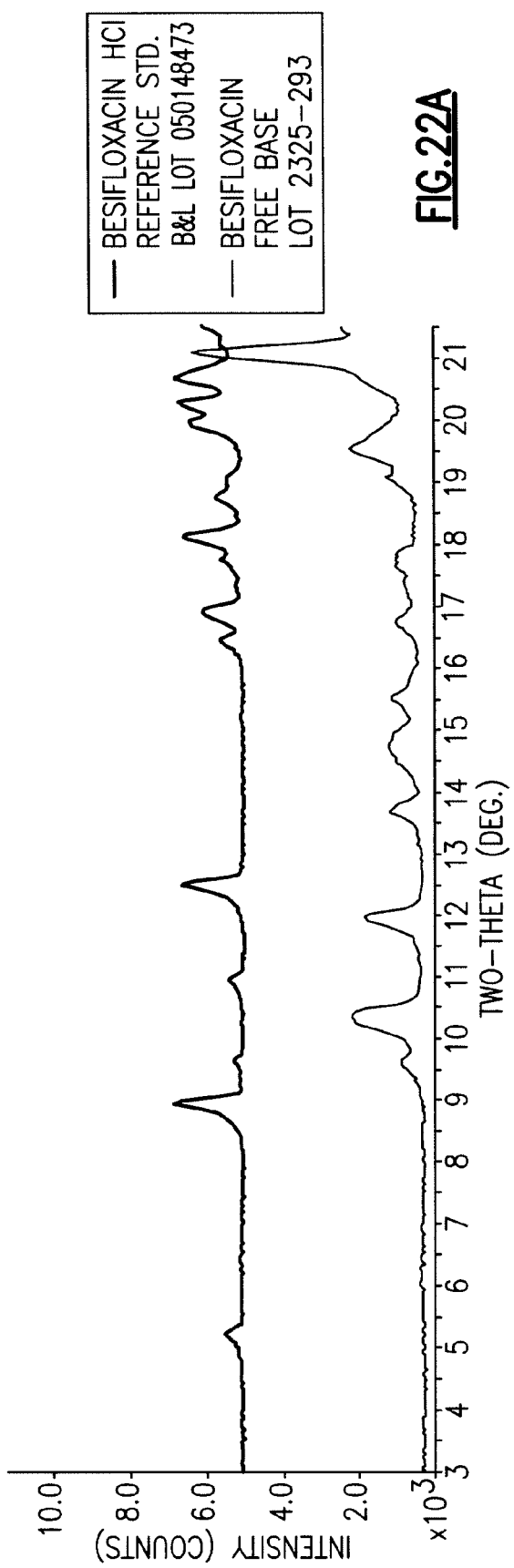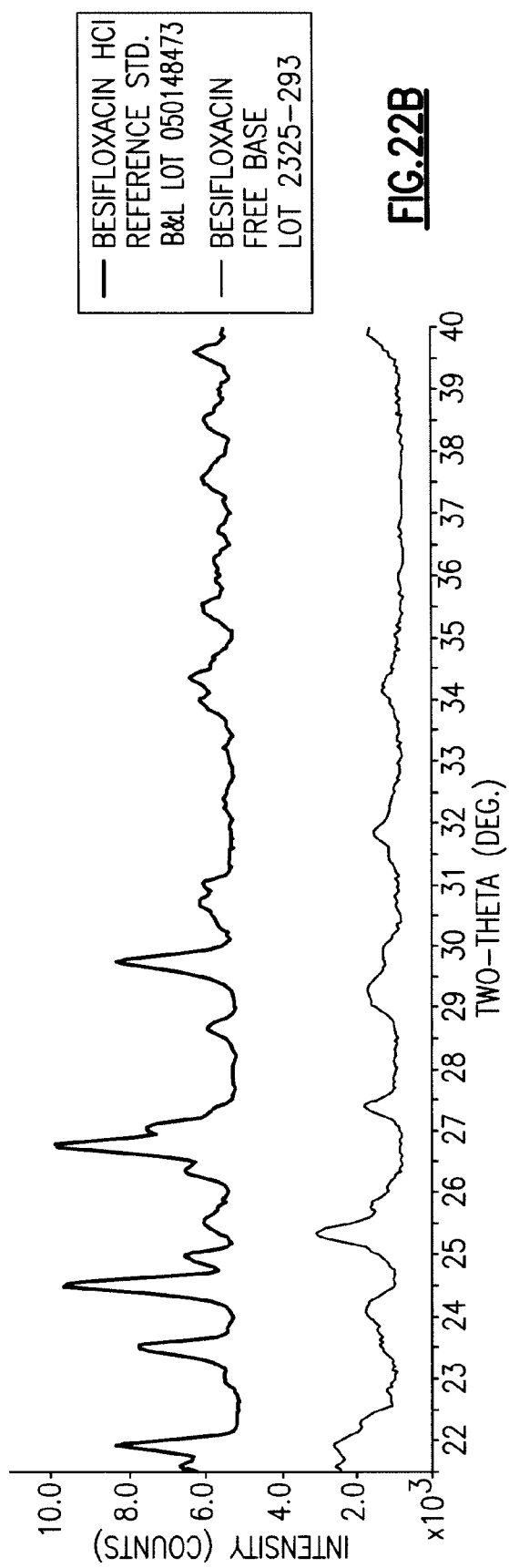

MAJOR DIFFRACTION PEAKS FOR BESIFLOXACIN FREE BASE
BASED ON ANALYSES ON 2009 FEBRUARY 26
A SINGLE PREPARATION OF LOT 2325-293 WAS
ANALYZED THREE TIMES. THE RESULTING THREE
PATTERNS WERE AVERAGED TO OBTAIN THE FOLLOWING.
EQUIPMENT: RIGAKU MINIFLEX WITH ASC-6 SAMPLE CHANGER
Cu k-alpha SOURCE, SAMPLE WAS SPUN DURING ANALYSIS

| ORDER OF PEAKS | DEGREES 2-THETA | d(Å) | HEIGHT (%) | TEN MOST INTENSE |
|---|---|---|---|---|
| 1 | 10.6 | 8.36 | 24.4 | 5 |
| 2 | 12.2 | 7.25 | 21 | 8 |
| 3 | 13.8 | 6.42 | 14.5 | 9 |
| 4 | 15 | 5.91 | 25 | 4 |
| 5 | 15.9 | 5.58 | 12.9 | |
| 6 | 16.7 | 5.30 | 7.8 | |
| 7 | 17.9 | 4.94 | 11.5 | |
| 8 | 19.1 | 4.65 | 5.8 | |
| 9 | 19.7 | 4.50 | 25.3 | 3 |
| 10 | 21.1 | 4.21 | 100 | 1 |
| 11 | 22 | 4.03 | 62.1 | 2 |
| 12 | 23.2 | 3.84 | 6.6 | |
| 13 | 23.9 | 3.71 | 11.3 | |
| 14 | 24.7 | 3.60 | 4.2 | |
| 15 | 25.5 | 3.49 | 23.8 | 6 |
| 16 | 25.9 | 3.43 | 26 | |
| 17 | 27.4 | 3.25 | 12.7 | |
| 18 | 28.2 | 3.16 | 5.1 | |
| 19 | 29.6 | 3.02 | 20.5 | 10 |
| 20 | 31.8 | 2.81 | 22.5 | 7 |
| 21 | 32.4 | 2.76 | 7.4 | |
| 22 | 34.2 | 2.62 | 3.6 | |
| 23 | 35.1 | 2.56 | 7.3 | |

FIG.25

| [0158.raw] Ref Std 14104J-3_40_pt05_1pt5perMi | Peak Search Report |
|---|---|

SCAN: 3.0/40.0/0.05/2(sec). Cu(30kV,15mA). I(max)=5192, 08/30/07 01:45p
PEAK: 17-pts/Quartic Filter. Threshold=3.0 Cutoff=0.1%. BG=1/1.0. Peak-Top=Summit
NOTE: Intensity=Counts,2T(0)=0.0(deg.).Wavelength to Compute d-Spacing=1.54059A (Cu/K-alpha1)

| # | 2-Theta | d(A) | BG | Height | H% | Area | A% | FWHM |
|---|---|---|---|---|---|---|---|---|
| 1 | 5.239 | 16.8551 | 300 | 433 | 9.4 | 2517 | 5.7 | 0.247 |
| 2 | 8.950 | 9.8724 | 265 | 1796 | 38.9 | 10826 | 24.4 | 0.256 |
| 3 | 9.636 | 9.1710 | 308 | 189 | 4.1 | 581 | 1.3 | 0.131 |
| 4 | 10.940 | 8.0807 | 256 | 369 | 8.0 | 2006 | 4.5 | 0.231 |
| 5 | 12.500 | 7.0755 | 249 | 1593 | 34.5 | 8923 | 20.1 | 0.238 |
| 6 | 15.214 | 5.8191 | 256 | 63 | 1.4 | 187 | 0.4 | 0.126 |
| 7 | 16.449 | 5.3846 | 314 | 536 | 11.6 | 3145 | 7.1 | 0.249 |
| 8 | 16.932 | 5.2322 | 356 | 969 | 21.0 | 5506 | 12.4 | 0.241 |
| 9 | 17.754 | 4.9918 | 386 | 447 | 9.7 | 2712 | 6.1 | 0.258 |
| 10 | 18.139 | 4.8866 | 392 | 1380 | 29.9 | 7716 | 17.4 | 0.238 |
| 11 | 18.758 | 4.7268 | 371 | 574 | 12.4 | 4405 | 9.9 | 0.326 |
| 12 | 20.283 | 4.3748 | 493 | 1436 | 31.1 | 11655 | 26.3 | 0.345 |
| 13 | 20.701 | 4.2873 | 588 | 1422 | 30.8 | 8529 | 19.2 | 0.255 |
| 14 | 21.606 | 4.1098 | 543 | 1341 | 29.1 | 17451 | 39.4 | 0.553 |
| 15 | 21.946 | 4.0468 | 480 | 3126 | 67.7 | 17981 | 40.6 | 0.244 |
| 16 | 23.049 | 3.8555 | 440 | 320 | 6.9 | 3666 | 8.3 | 0.486 |
| 17 | 23.535 | 3.7771 | 493 | 2518 | 54.6 | 16861 | 38.0 | 0.285 |
| 18 | 24.507 | 3.6295 | 576 | 4372 | 94.7 | 23924 | 54.0 | 0.233 |
| 19 | 24.982 | 3.5615 | 612 | 1188 | 25.7 | 5879 | 13.3 | 0.210 |
| 20 | 25.543 | 3.4845 | 642 | 670 | 14.5 | 4492 | 10.1 | 0.285 |
| 21 | 26.355 | 3.3789 | 733 | 1043 | 22.6 | 11018 | 24.9 | 0.449 |
| 22 | 26.791 | 3.3250 | 576 | 4616 | 100.0 | 44314 | 100.0 | 0.408 |
| 23 | 28.038 | 3.1798 | 457 | 73 | 1.6 | 351 | 0.8 | 0.205 |
| 24 | 28.657 | 3.1126 | 452 | 725 | 15.7 | 4258 | 9.6 | 0.250 |
| 25 | 29.748 | 3.0009 | 580 | 3006 | 65.1 | 18781 | 42.4 | 0.266 |
| 26 | 30.464 | 2.9319 | 618 | 340 | 7.4 | 6544 | 14.8 | 0.818 |
| 27 | 31.031 | 2.8796 | 581 | 709 | 15.4 | 8085 | 18.2 | 0.485 |
| 28 | 32.401 | 2.7609 | 517 | 228 | 4.9 | 1563 | 3.5 | 0.291 |
| 29 | 33.191 | 2.6970 | 523 | 233 | 5.1 | 764 | 1.7 | 0.139 |
| 30 | 33.996 | 2.6350 | 524 | 866 | 18.8 | 12979 | 29.3 | 0.637 |
| 31 | 34.350 | 2.6086 | 519 | 1152 | 25.0 | 15321 | 34.6 | 0.565 |
| 32 | 35.534 | 2.5243 | 561 | 735 | 15.9 | 8038 | 18.1 | 0.465 |
| 33 | 36.277 | 2.4743 | 679 | 315 | 6.8 | 3683 | 8.3 | 0.496 |
| 34 | 36.738 | 2.4443 | 634 | 219 | 4.7 | 803 | 1.8 | 0.156 |
| 35 | 37.594 | 2.3906 | 610 | 701 | 15.2 | 6355 | 14.3 | 0.385 |
| 36 | 38.503 | 2.3363 | 628 | 622 | 13.5 | 5414 | 12.2 | 0.370 |
| 37 | 38.995 | 2.3079 | 641 | 227 | 4.9 | 1686 | 3.8 | 0.315 |

TWO-THETA (deg)

US 8,481,526 B2

FLUOROQUINOLONE CARBOXYLIC ACID MOLECULAR CRYSTALS

CROSS REFERENCE

This application claims the benefit of Provisional Patent Application No. 61/163,223 filed Mar. 25, 2009 which is incorporated by reference herein.

BACKGROUND OF THE INVENTION

The present invention relates to fluoroquinolone carboxylic acid molecular crystals. In particular, present invention relates to a molecular crystal of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid.

Synthetic antimicrobial agents such as nalidixic acid, piromidic acid, and the like are known as drugs for curing infectious diseases caused by Gram negative microorganisms. They exhibit, however, only deficient effects on intractable diseases such as pseudomoniasis and the like.

On the other hand, quinolone carboxylic acid derivatives substituted with a fluorine atom at 6 position, such as norfloxacin, ofloxacin, and ciprofloxacin, or quinolone carboxylic acid derivatives substituted with a chlorine atom at 8 position have been developed (Japanese Patent Laid-open (ko-kai) Nos. 225181/1986, 90183/1989) and clinically used because of their strong antimicrobial activity.

These conventional synthetic antimicrobial agents had defects of insufficient absorptivity in a living body, providing only low bioavailability, and of a low antimicrobial activity against Gram positive microorganisms.

Therefore, development of antimicrobial agents having strong antimicrobial activity against both Gram positive and Gram negative microorganisms, including resistant bacteria, and superior absorptivity in living bodies has been desired.

Active pharmaceutical agents ("APIs") are often organic molecules, which can exist in different organic crystal forms depending on their processes of manufacture. Such different molecular crystal forms can have practical influence on pharmaceutical compositions comprising these APIs, such as their processability, physical and chemical properties, stability, etc.

Therefore, it is desirable to provide a molecular crystal form of the API that has advantageous properties. In particular, it is very desirable to provide a molecular crystal form of a fluoroquinolone carboxylic acid that has advantageous properties for the manufacture of novel anti-infective pharmaceutical compositions.

SUMMARY

In general, the present invention provides a specific molecular form of a fluoroquinolone carboxylic acid.

In one aspect, the present invention provides a specific molecular form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid.

In another aspect, the present invention provides a stable molecular form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid.

In still another aspect, the present invention provides a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2

In yet another aspect, the present invention provides a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by a DSC (differential scanning calorimetry) melting peak at 288° C.

In a further aspect, the present invention provides a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by $^{13}C$ NMR spectrum having peaks at 23.3, 27.7, 41.1, 54.5, 116.6, and 153.5 ppm.

In still another aspect, the present invention provides a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by pKa values of 5.65 and 9.91.

In yet another aspect, the present invention provides a pharmaceutical composition comprising a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°; or by a DSC melting peak at 288° C.; or by a $^{13}C$ NMR spectrum having peaks at 23.3, 27.7, 41.1, 54.5, 116.6, and 153.5 ppm; or by pKa values of 5.65 and 9.91.

In a further aspect, the present invention provides a pharmaceutical composition comprising a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°; a DSC melting peak at 288° C.; and a $^{13}C$ NMR spectrum having peaks at 23.3, 27.7, 41.1, 54.5, 116.6, and 153.5 ppm.

In still another aspect, the present invention provides a pharmaceutical composition comprising a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°; a DSC melting peak at 288; a $^{13}C$ NMR spectrum having peaks at 23.3, 27.7, 41.1, 54.5, 116.6, and 153.5 ppm; and pKa values of 5.65 and 9.91.

Other features and advantages of the present invention will become apparent from the following detailed description and claims and the appended drawings.

BRIEF DESCRIPTION OF THE DRAWINGS

A brief description accompanies each figure shown below.

FIG. 7A shows the X-ray powder diffraction ("XRPD") analysis summary for besifloxacin HCl salt, Lot 051157469.

FIG. 8A shows the X-ray powder diffraction analysis summary for besifloxacin free base, Lot 2325-293.

FIGS. 22A and 22B show the X-ray powder diffraction analysis patterns of besifloxacin HCl reference standard and besifloxacin free base.

FIG. 25 shows a table of majors X-ray powder diffraction analysis peaks of besifloxacin free base.

DETAILED DESCRIPTION OF THE INVENTION

As used herein, the term "control" also includes reduction, alleviation, amelioration, and prevention.

As used herein, the term "stable" means incapable of changing in crystalline structure, as exhibited by a plurality of peaks in an XRPD pattern, at a time of two weeks after the initial preparation of the material.

In general, the present invention provides stable molecular crystal of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid.

Throughout the present disclosure and claims, (R)-(+)-7-(3-amino-2,3,4,5,6,7-hexahydro-1H-azepin-1-yl)-±1-cyclopropyl-8-chloro-6-fluoro-1,4-dihydro-4-oxoquinoline-3-carboxylic acid is also referred to as besifloxacin.

Synthesis of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid is disclosed in U.S. Pat. No. 5,447,926, which is incorporated herein by reference in its entirety.

Besifloxacin HCL salt (the HCl addition salt of besifloxacin) was observed to be sparingly soluble in water, slightly soluble in methanol and ethanol and insoluble in acetonitrile and isopropanol. Besifloxacin has two ionizable functional groups throughout the pH range from 2-12, namely, a carboxylic acid and a primary amine. The ionization of these functional groups from pH 5.5-9.0 results in formation of a zwitterion, which crystallizes as a very slightly soluble (about 0.1 mg/mL) solid. Hence, besifloxacin HCl was observed to convert in aqueous media (pH>4) to a new crystalline phase that was free of counterions (hereafter referred to as "free base"). Independent spectroscopic investigations confirm that the free base is a zwitterionic molecular crystal. At pH>9 and pH<5, the solubility of besifloxacin increased to maximum of about 10 mg/mL (pH 3) as a function of pH. The pH-solubility profile was fitted to the Henderson-Hasselbach equation, assuming an intrinsic solubility of 0.074 mglmL, and the pKas of the carboxylic and primary amine groups were estimated as 5.65 and 9.91, respectively.

Unique powder X-ray diffraction (XRPD) patterns were identified for both the besifloxacin free base and HCl salt. These forms also had unique melting temperatures, as detected by DSC (differential scanning calorimetry). The free base was observed to have a peak melt at 288° C., as compared to 321.5° C. for the HCL salt. Melting of both solids was attended by decomposition. Based on XRPD analysis of drug product, no evidence of the HCl salt was observed, however, peaks associated with the free base were consistently present. In solution at pH 6.5 (product pH), the free base of besifloxacin had the lowest solubility. Therefore, it is likely that all HCl salt converts to the free base during product manufacture. These studies indicate that the free base of besifloxacin is the dominant crystalline phase in the drug product.

Figure 1:
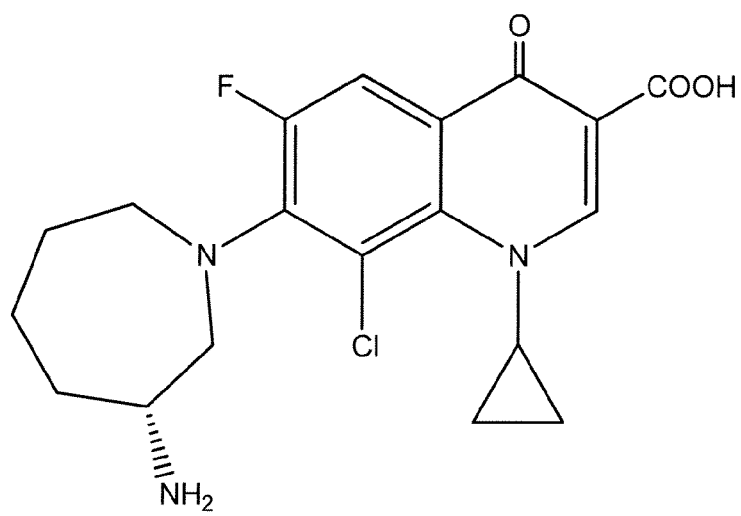
FIG. 1 shows the structure of besifloxacin.

Besifloxacin is a fluorochloroquinolone that is currently being developed as an antibiotic for treatment of eye infections. Pharmaceutical products are manufacture with the HCl addition salt of besifloxacin as the strating material of the active pharmaceutical ingredient ("API"). Besifloxacin HCl salt, with a molecular weight of 430. The structure of besifloxacin HCL is shown in FIG. 1. The physico-chemical properties of besifloxacin HCl salt were studied and the solid phase containing besifloxacin in the pharmaceutical composition was elucidated.

Besifloxacin HCl salt lots 050956330 and 051157469 were used to formulate the pharmaceutical compositions. Both lots are considered representative of material used to fonnulate drug product used in many studies, and met all specifications. Additionally, several laboratory lots of free base were prepared using methods described below. These batches were designated by numbers as 2325-293, 2325-288, and 2325-282.

Instruments

Burrell Wrist Action Shaker, model 75

Chromatographic systems: HP 1100 with photodiode array detectory. HP chemstation software Differential Scanning Calorimeter (DSC), Perkin Elmer, Pyris Mettler Balance, Model AE160

Accumet 925 pH/ion meter

Rigaku Miniflex XRPD unit CuK alpha source (30 kVI15 mA)

Thermogravimetric analyzer, TA Instruments

Moisture Sorption analyzer, model MB-300W, VTI corporation

High Performance Liquid Chromatography (HPLC) Method

A reversed phase gradient HPLC method was used for the analysis of besifloxacin solubility samples. The conditions are listed below:

| Besifloxacin gradient HPLC method | | | | |
|---|---|---|---|---|
| Column | YMC-PACK Pro, C18, 3 µm, 50 mm × 4.6 mm | | | |
| Mobile phase | A. 0.05% v/v trifluoroacetic acid in water B. 0.05% v/v trifluoroacetic acid in acetonitrile | | | |
| Flow rate | 1.0 mL per minute | | | |
| | Time (min.) | % A | % B | Transition |
| Gradient Table | Initial | 99 | 1 | Linear |
| | 1 | 99 | 1 | Linear |
| | 20 | 1 | 99 | Linear |
| | 21 | 99 | 1 | Linear |
| | 30 | 99 | 1 | Linear |
| Detector | UV-Photodiode Array Detector: 200 to 360 nm with 4.8 nm resolution and acquisition rate of 1 spectrum per second. | | | |
| Wavelength extracted | 289 nm | | | |
| Column temperature | Ambient (24 ± 3° C.) | | | |
| Run time | 30 minutes | | | |
| Typical retention time of besifloxacin | 10.3 minutes | | | |
| Diluent | 0.07% phosphoric acid | | | |

The solubility of besifloxacin HCl was evaluated in several organic solvents. An excess of drug substance was equilibrated with 10 mL of each solvent for 24-48 hours at room temperature (24±3° C.) using either a small magnetic stirrer or a Burrell Wrist Action shaker. Samples were inspected visually, and if needed, more drug substance was added until excess solid persisted after stirring. The samples were then filtered through 0.45 µm Nylon or PVDF filters or centrifuged at 10,000 RPM for 15 minutes. The filtrate or the supernatant was diluted as needed using the HPLC diluent and analyzed by HPLC. When solubility was greater than 100 mg/mL, no attempt was made to determine the equilibrium solubility and the compound was described as "freely soluble" as per the USP definition.

The solubility of besifloxacin HCl, lot 050956330, was determined in distilled water as a function of pH by adjusting the pH with 1 N NaOH. Suspensions of the drug substance (about 50-150 mg in 10 mL distilled water) were equilibrated for 72-96 hours using a Burrell shaker. Laboratory temperature was 22±2° C. The pH of the suspensions was measured in the presence of excess solid prior to sampling. The samples were centrifuged in an Enprotech ISS-I13 centrifuge at 10,000 RPM for 15 minutes or filtered through 0.45~Nylon or PVDF filters. When samples were filtered, a volume of filtrate was discarded to allow saturation of filters. The supernatant or the filtrate was diluted as needed using the HPLC diluent prior to analysis. Sample concentration was monitored at varying time intervals to ensure complete equilibration. Also, sample concentration was reported as besifloxacin free base concentration rather than HCl salt.

To determine pKas that were consistent with observed solubility behavior, the pH dependent solubility was fitted to the following expression:

$$S = S_o * (10^{pKa1-pH} + 10^{pH-pKa2} + 1)$$

where S=solubility $S_o$=intrinsic solubility (total of zwitterionic and neutral species)

$pK_{a1}$=dissociation constant for the carboxylic acid moiety $pK_{a2}$=dissociation constant for the primary ammonium ion moiety Differential Scanning Calorimetry (DSC) and Thermogravimetric Analysis (TGA)

DSC experiments were performed on a Perkin-Elmer Pyris 7 DSC and results were analyzed with Pyris Software, version 7.0.0.0110. A small amount of finely ground powder was accurately weighed (about 1.5-3 mg) into a 50 µL aluminum pan. The pan was crimp sealed with a pinhole cover. Samples were scanned from 50° C. to 340° C. at 20° C./min. The onset of melting for the solid was extrapolated from the melting curve. Additionally, other events were recorded, such as exotherms on decomposition, to characterize this material.

For thermogravimetric analysis, a TA Instruments Model Q50 was used. A sample, weighing approximately 15 mg was loaded onto a tared platinum holder. The sample was heated from room temperature to 350° C. at 10°/minute. During the heating, the sample was flushed with nitrogen at 40 mL/min. Weight loss of the sample was monitored as a function of temperature.

Moisture Sorption Analysis

Moisture uptake and loss was monitored as a function of relative humidity using a VTI, moisture sorption balance. A 30-40 mg sample was loaded into a tared glass sample holder. The initial weight of the sample was accurately recorded. The sample was then dried under a steady stream of nitrogen for 2 hours at 40° C. After initial drying, the sample mass was equilibrated with dry nitrogen at 25° C. and the sample was exposed to progressive stepwise increases in humidity under controlled conditions. The sample was equilibrated for two hours at each new relative humidity. The moisture sorption behavior was monitored at 10% to 90% RH in 10% RH intervals and desorption was monitored from 90% to 10% RH. The % moisture gain/loss was recorded vs. the % RH.

Preparation of Solid Besifloxacin Free Base

The free base of besifloxacin was isolated by dissolving the HCl salt in water and adjusting the pH to >10 with 1 N NaOH. The pH of the solution was gently lowered to ~9-10 with 1 N HCl. The resulting slurry was agitated for 1 hour at room temperature and the precipitate was isolated via filtration using a membrane filter. The solid was dried in a vacuum oven at room temperature for 24-48 hours.

Powder X-Ray Diffraction

Approximately 20-100 mg of powder was loaded onto a low background sample holder. Samples were analyzed on a Rigaku Miniflex (scanning configuration) and scanned from 5-60°, 2-theta at a rate of 1°2θ/minute with a sampling rate of 0.02 seconds. Patterns were analyzed using Jade software version 7.5, provided by Materials Data Inc.

Analysis of Crystalline Solids in Besifloxacin Ophthalmic Suspension (0.6 mg/g)

The besifloxacin suspension formulation is a viscous solution containing a suspension of solid drug particles in hydrated polycarbophil. Attempts to isolate the solids by filtration or centrifugation were unsuccessful. To determine the crystalline phase of besifloxacin in the suspension formulation, approximately 5 grams of suspension were dried in vacuum oven at RT. Samples were taken from multiple batches (ISV Lots J04Q, E06Q, 965701, E04Q, and D05Q) to assess batch-to-batch consistency. After drying, the material was crushed in a mortar and analyzed by XRPD. The sensitivity of this method for solid besifloxacin HCl was investigated by spiking 5-20% w/w besifloxacin HCl salt into the dried placebo (lot AAP-020). These mixtures were analyzed by XRPD to determine the lowest concentration of besifloxacin HCl that could be detected.

Results

Solubility

The solubilities of besifloxacin HCl salt and free base (Lot 2325-293) are presented in the Table 1. Excess solids were isolated from equilibrated samples and analyzed by XRPD. In organic solvents, no form conversions were observed. In the aqueous pH solubility samples however, the excess besifloxacin HCl solid was converted to a different crystalline phase at pHs>3.5-4.0. As discussed below (XRPD section), this phase was identified as the crystalline besifloxacin free base.

Figure 2:
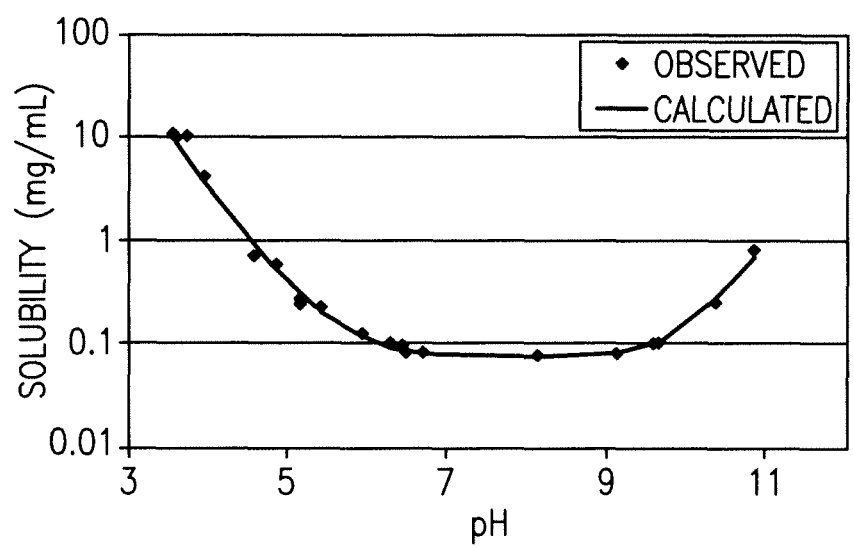
FIG. 2 shows the pH-solubility profile of besifloxacin HCl, Lot 050956330.

Besifloxacin is an ionizable compound, containing both a carboxylic acid and a primary amine, and both of these ionizable groups contribute to the observed solubility behavior in an aqueous medium. The solubility values are tabulated as a function of pH in Table 2. This data was satisfactorily fit to the Henderson-Hasselbach equation. To achieve the best fit, the $pK_a$ values of the carboxylic acid and primary ammonium groups were estimated as 5.65 and 9.91, respectively, and the intrinsic solubility ($S_o$) was estimated at 0.074 mg/mL. The experimental data and the fitted curve is shown in FIG. 2. As shown in FIG. 2, the solubility of the molecule is relatively constant (about 0.1 mg/mL) throughout the pH range of 5.5-9, where both the carboxylic acid and primary amine functional groups are ionized. Hence the "free base" of besifloxacin is actually the solid that precipitates from a poorly soluble zwitterion, resulting from deprotonation of the carboxylic acid in besifloxacin HCl. Deprotonation of the carboxylic acid becomes significant enough for the besifloxacin free base to dominate the solubility equilibrium in aqueous solutions at pHs exceeding about 3.5. At both acidic pH (pH<5) and alkaline pH (pH>9), the solubility of besifloxacin free base increases as the doubly-charged but neutral zwitterion equilibrates with singly ionized species as a function of the pH in the range around the $pK_a$s of either the carboxylic acid or the primary amine.

Figure 3:
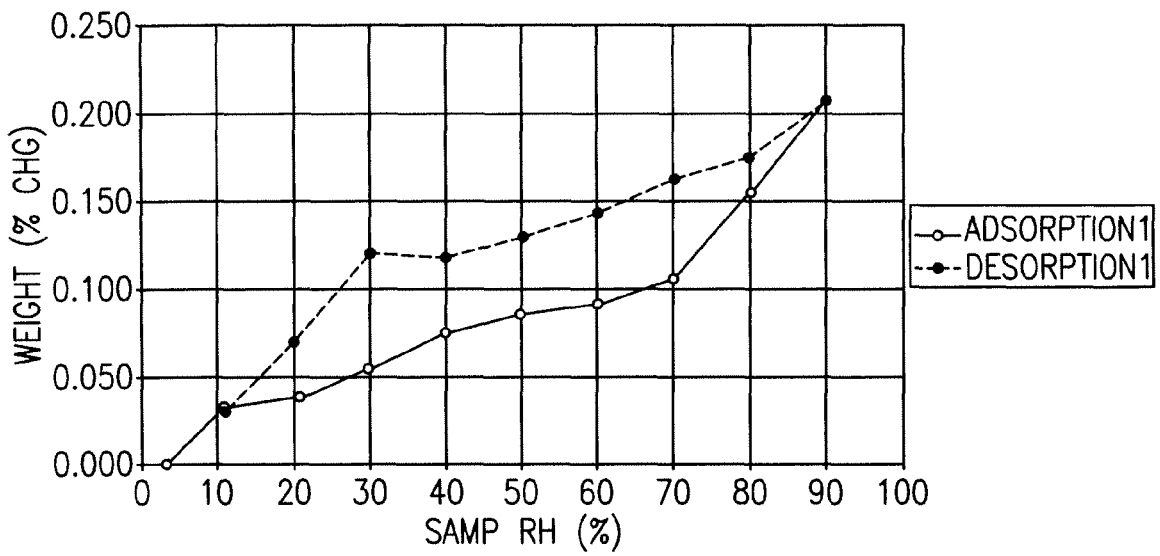
FIG. 3 shows the moisture sorption of besifloxacin HCl salt, Lot 050956330.
Figure 4:
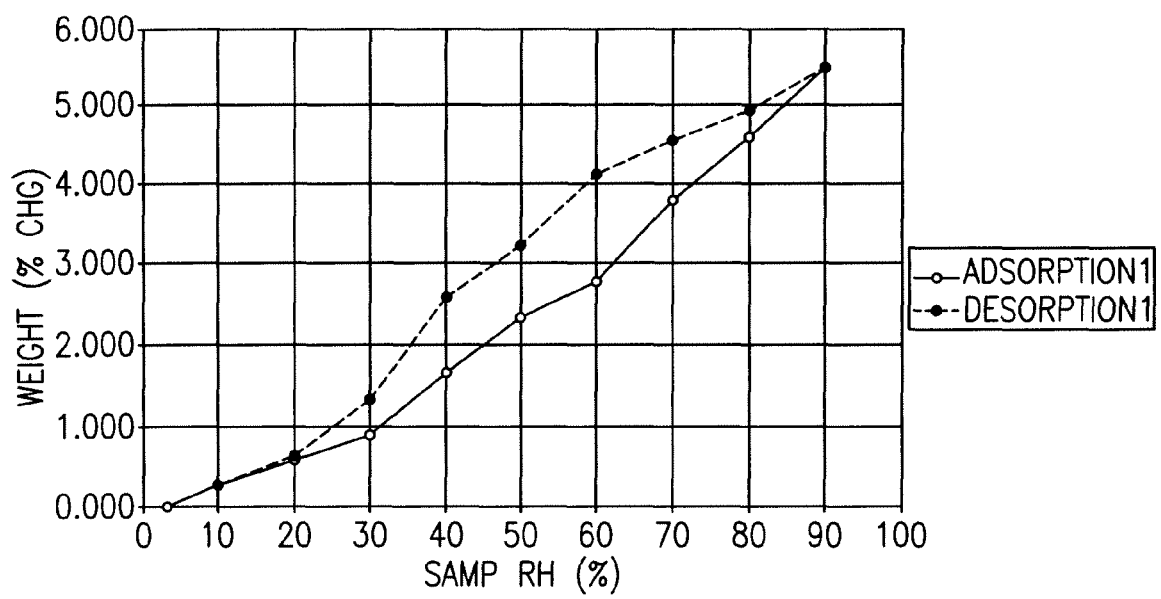
FIG. 4 shows the moisture sorption of besifloxacin free base, Lot 2325-288.

Moisture Sorption Analysis of Besliflocaxin HCl:

The moisture sorption data for besifloxacin HCl, lot 050956330 and besifloxacin free base, lot 2325-288, are shown in FIGS. 3 and 4, respectively. Besifloxacin HCl was not hygroscopic. Besifloxacin free base sorbed moisture at all RH conditions, and up to 5% w/w at 90% RH.

Figure 5A:
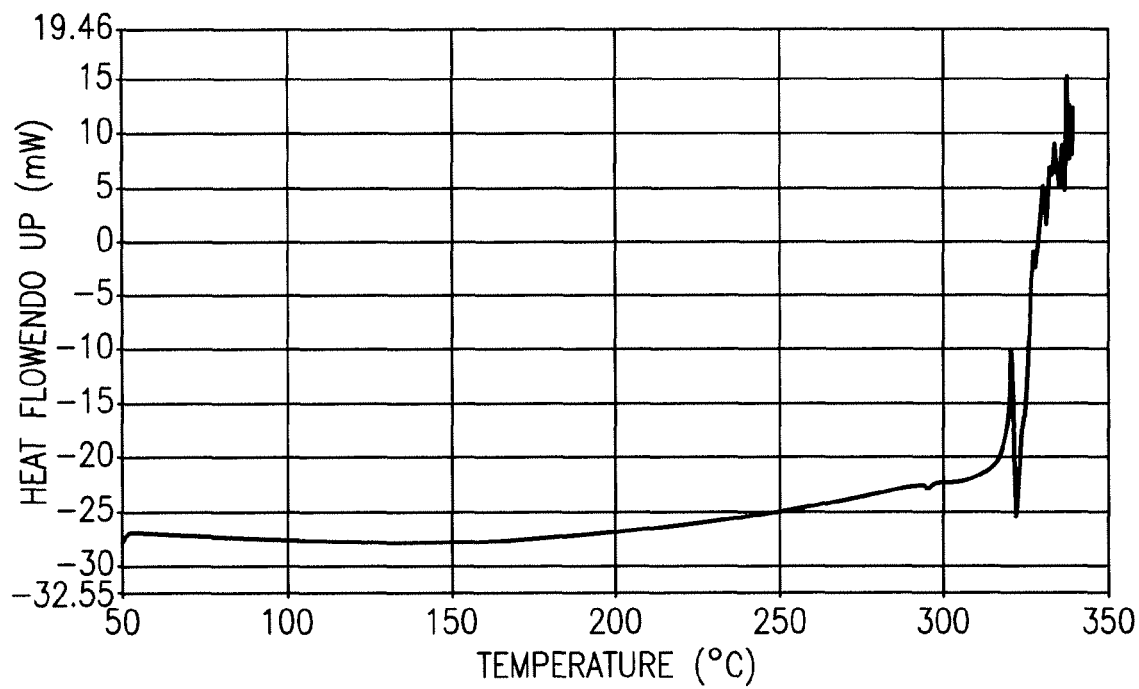
FIG. 5A shows the differential scanning calorimetry ("DSC") scan for besifloxacin HCl, Lot 051157469.
Figure 5B:
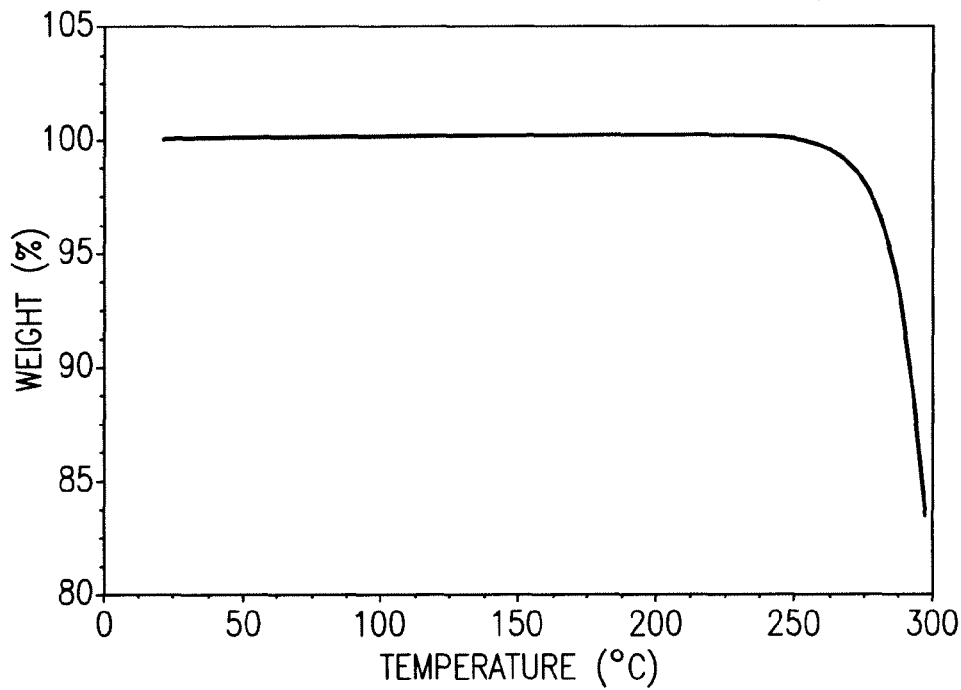
FIG. 5B shows the thermal gravimetric analysis ("TGA") scan for the same.

Thermal Analysis of Besifloxacin HCl and Besifloxacin Free Base:

The result of differential scanning calorimetry (DSC) for a typical sample of besifloxacin HCl (lot 051157469) is shown in FIG. 5A. The profile shows an endotherm corresponding to melting with an extrapolated onset temperature of 315.7° C. The peak melt temperature and integrated values for heat of fusion could not be determined because the melting endotherm was interrupted by a sudden irregular exotherm/endotherm, which appeared to result from attendant decomposition of the melt phase.

TGA in the open pan showed significant weight loss prior to melting for the HCl form as shown in FIG. 3. As expected, there was no evidence of sudden weight loss events that would be associated with solvated or hydrated solids. The mass loss that occurred above the melt temperature was consistent with the supposition that melting was attended by decomposition. The mass loss below the melt temperature may be associated with the dehydrochlorination.

Figure 6A:
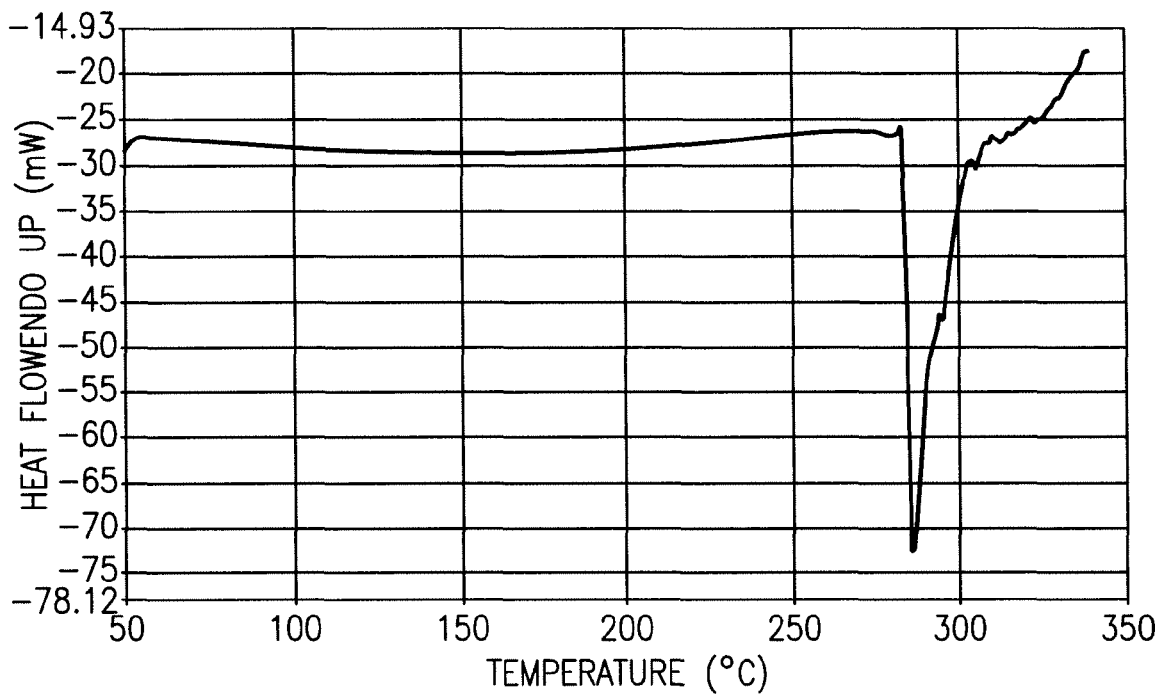
FIG. 6A shows the differential scanning calorimetry scan of besifloxacin free base, lot 2325-282-0.
Figure 6B:
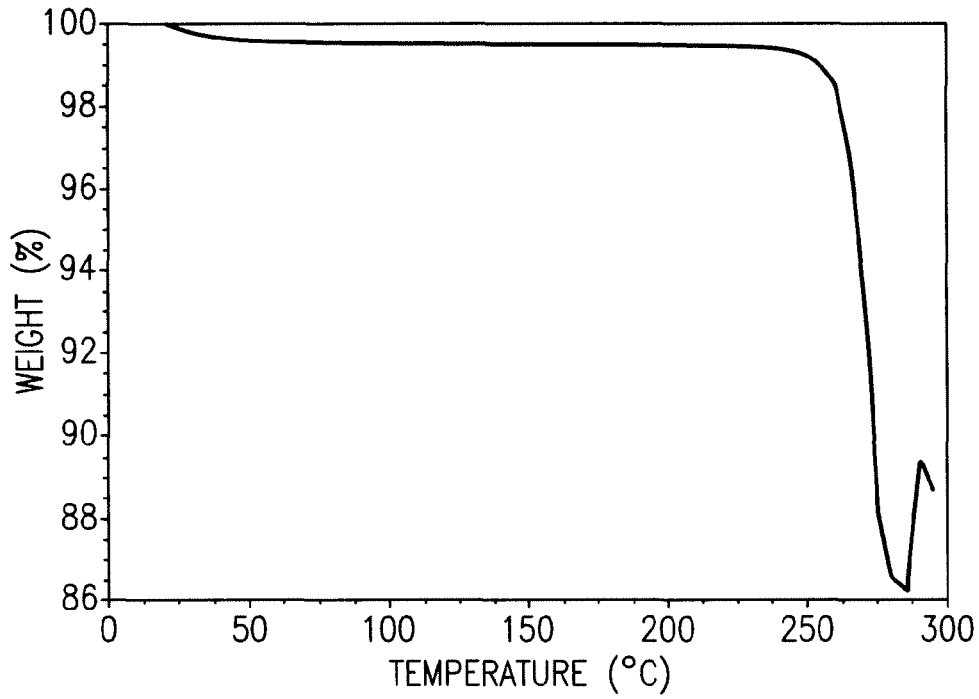
FIG. 6B shows the thermal gravimetric analysis scan of the same.

Crystalline besifloxacin free base was isolated from pH solubility experiments (Lot 2325-282) and analyzed by DSC. This material had a peak melting temperature of 288.1° C. with an extrapolated onset melting temperature of 279.0° C. as shown in FIG. 6A. There were additional thermal events at temperatures above the peak melting temperature, probably as a result of thermal decomposition. The heat of fusion integrals were variable because this thermal event was not resolved from the melting transition. Thermogravimetric data, shown in FIG. 6B, showed a slight weight loss prior to melting that varied between runs from 0.3-0.6%. In terms of magnitude and temperatures of onset, this weight loss profile was more characteristic of sorbed water and not typical of the type of weight loss associated with stoichiometric hydrates.

X-Ray Powder Diffraction Analysis ("XRPD")

Figure 7B:
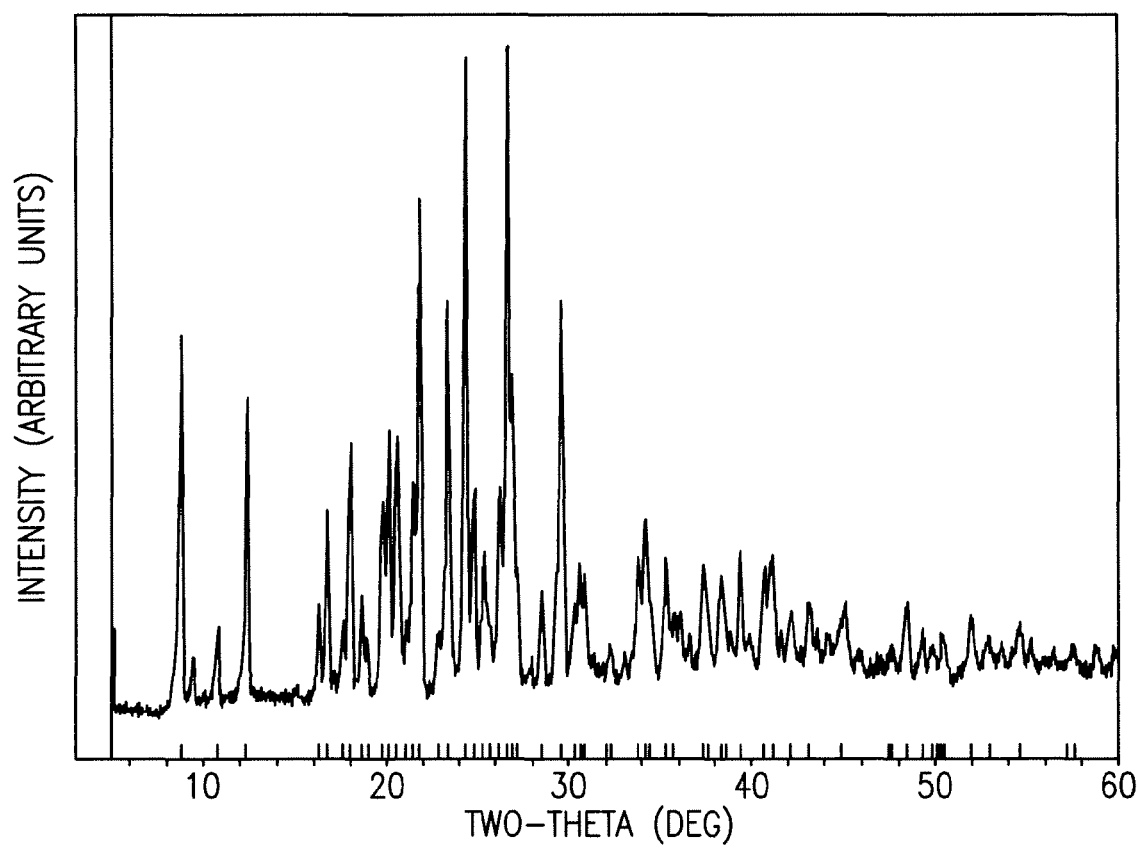
FIG. 7B shows the XRPD pattern of the same, showing the peaks listed in the table of FIG. 7A.
Figure 8B:
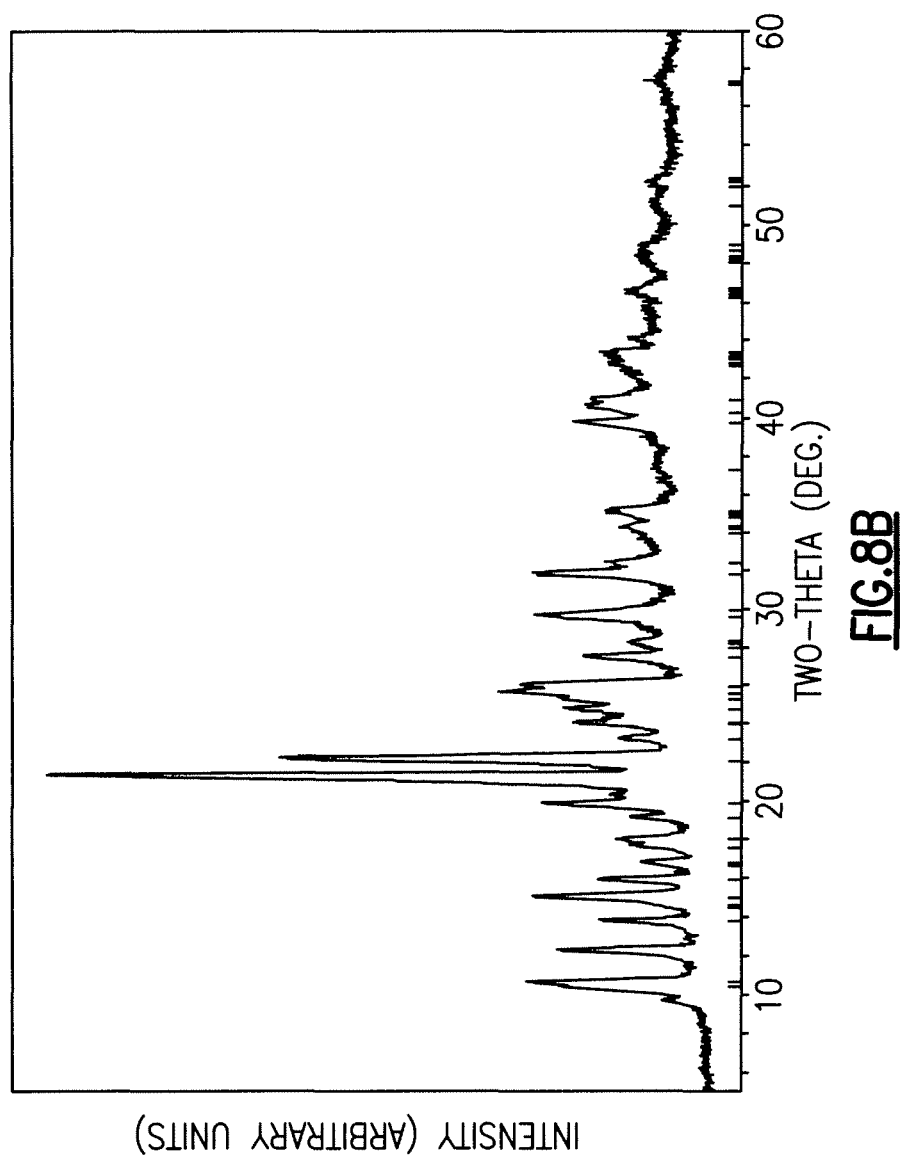
FIG. 8B shows the XRPD pattern of the same, showing the peaks listed in the table of HG. 8A.
Figure 9:
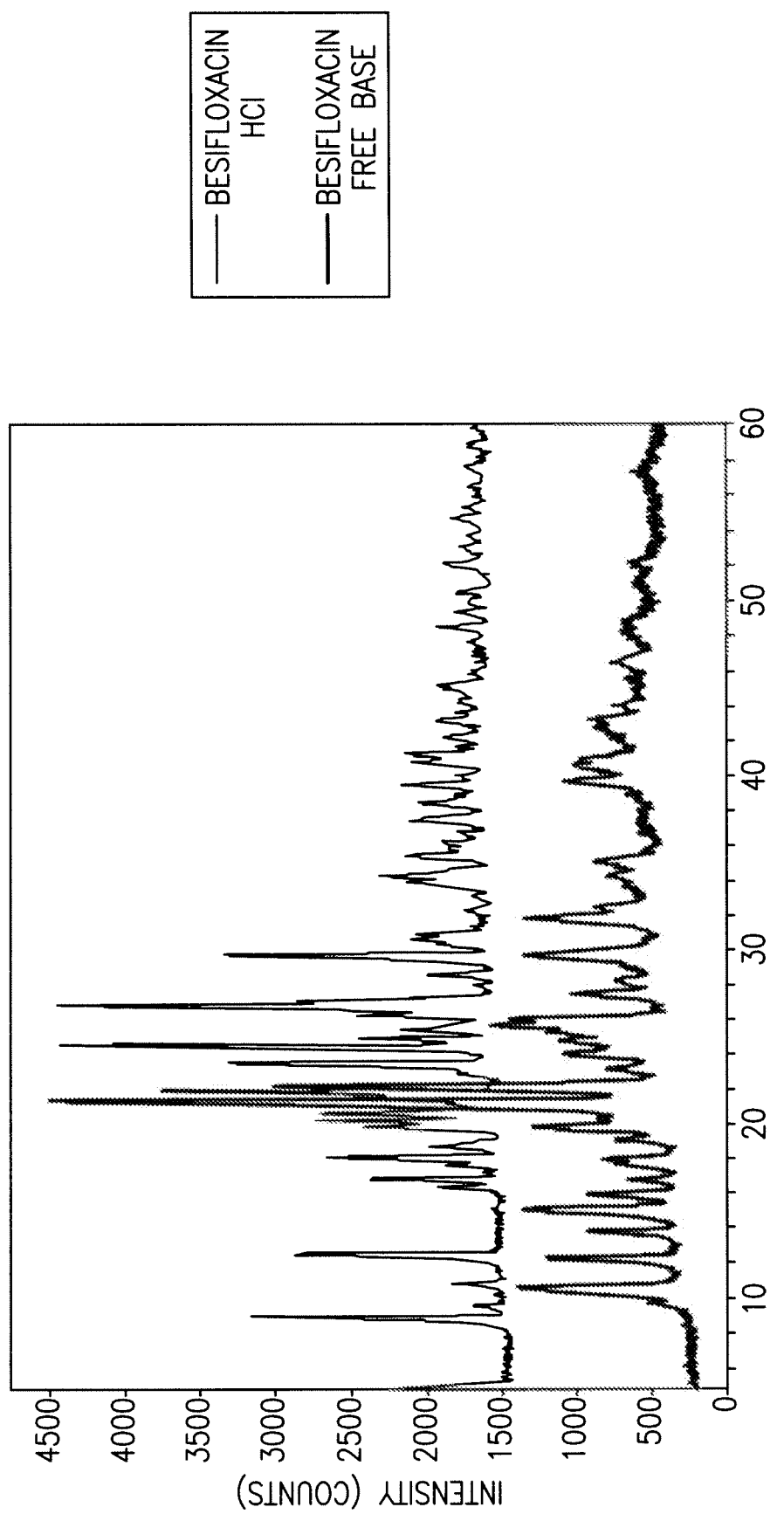
FIG. 9 shows the overlay of X-ray powder diffraction analysis patterns for besifloxacin HCl salt and free base.

Unique XRPD patterns were observed for besifloxacin HCl (Lot 051154769) and besifloxacin free base (Lot 2325-293). See FIGS. 7B and 8B. The peak listing for each of these samples is provided in FIGS. 7A and 8A. An overlay of their diffraction patterns is shown in FIG. 9.

Figure 10:
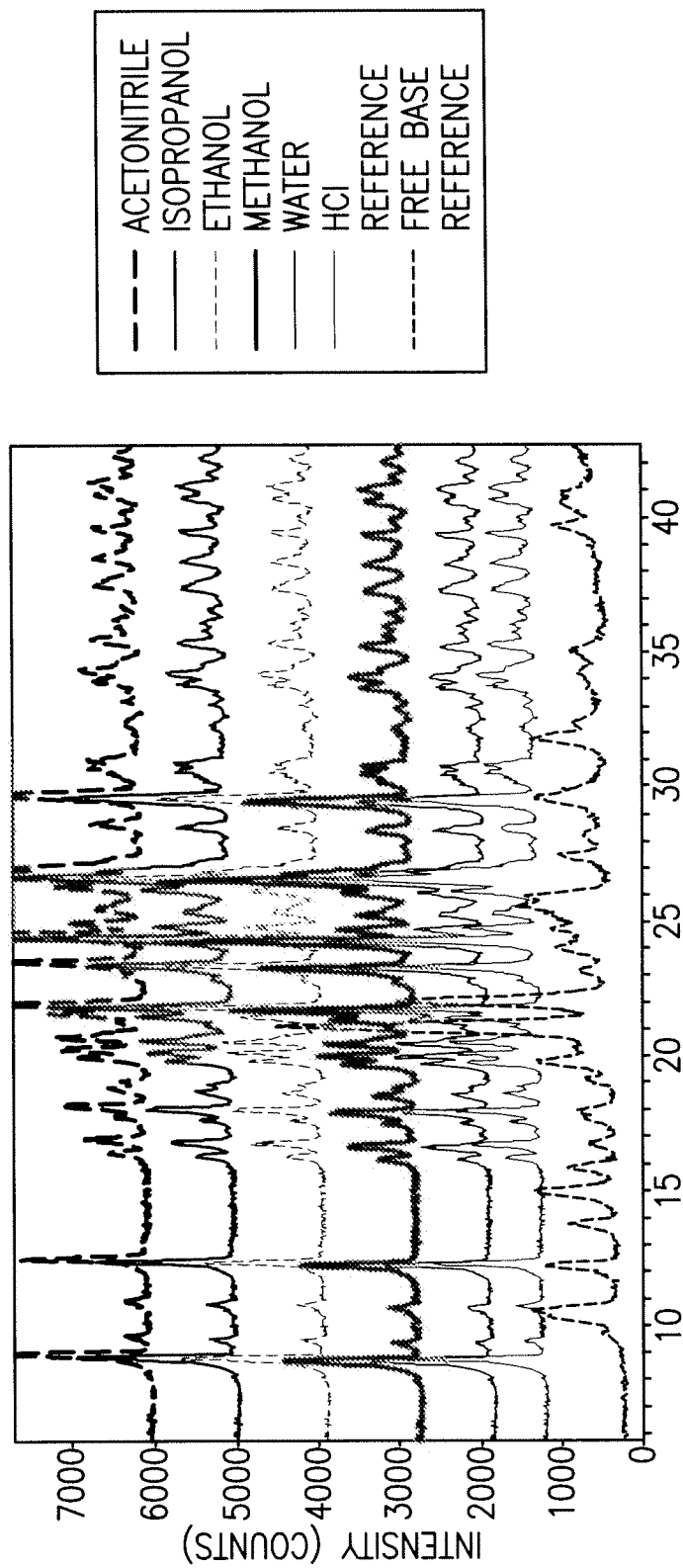
FIG. 10 shows the X-ray powder diffraction analysis patterns of excess solids obtained from organic solvent equilibrium samples (besifloxacin HCl salt).
Figure 11:
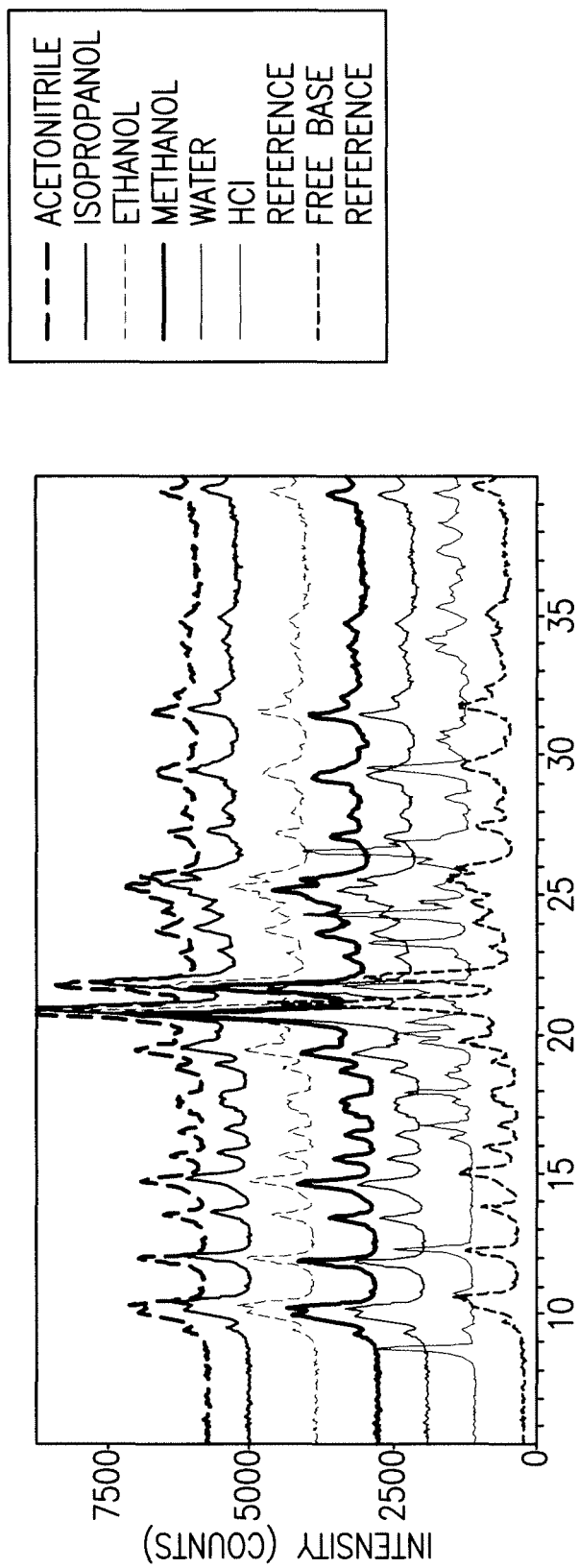
FIG. 11 shows the X-ray powder diffraction analysis patterns of excess solids obtained from organic solvent equilibrium samples (besifloxacin free base).

The XRPD patterns of the excess solid equilibrated in methanol, ethanol, acetonitrile, isopropanol and water are shown in FIG. 10 for besifloxacin HCl and FIG. 11 for besifloxacin free base XRPD of solids from Besifloxacin Ophthalmic Suspension (0.6%)

Figure 12:
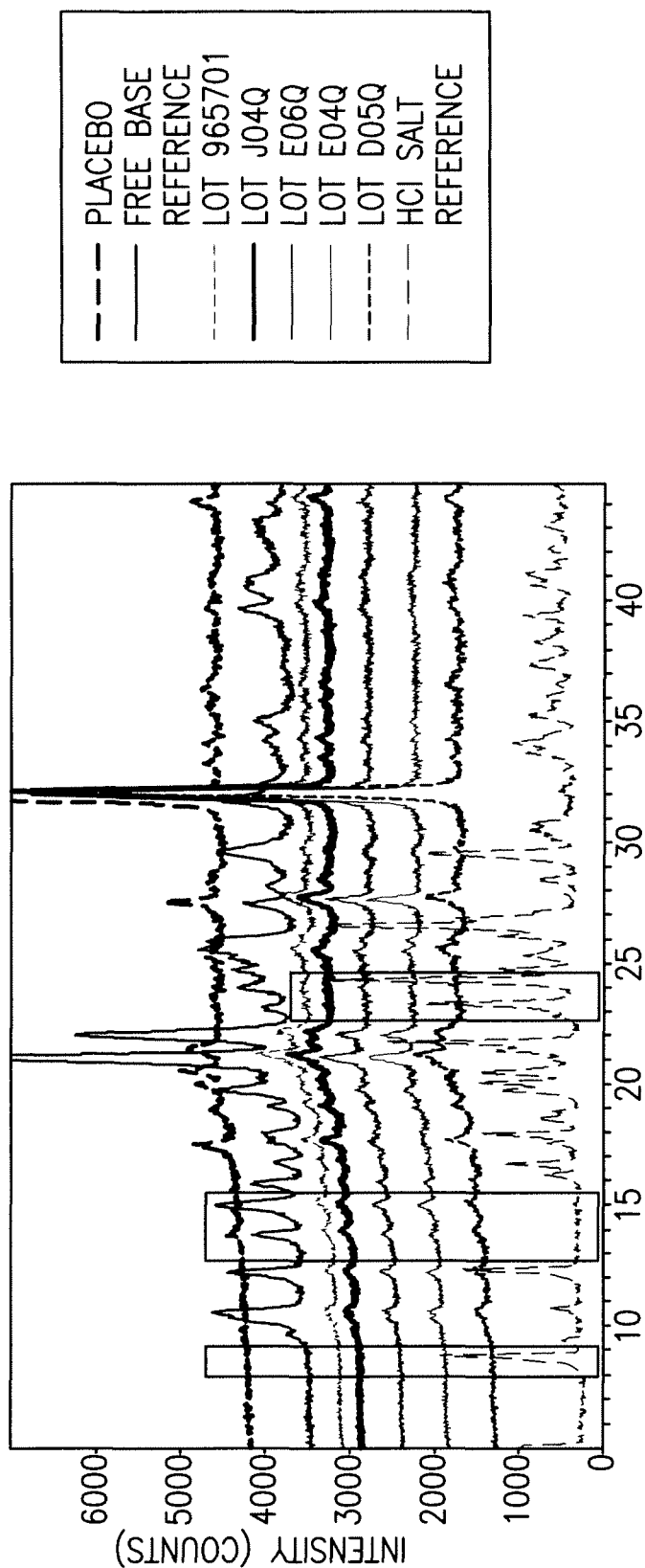
FIG. 12 shows X-ray powder diffraction analysis identification of besifloxacin free base in formulated besifloxacin ophthalmic suspension (0.6%).

XRPD analysis of besifloxacin ophthalmic suspension (0.6%) of lots 965701, J04Q, E04Q, E06Q and D05Q consistently showed diffraction peaks corresponding to besifloxacin free base, and absence of detectable peaks from besifloxacin HCl. Diffraction patterns are shown in FIG. 12. The age of these batches at the time of analysis was between 17-25 months, as summarized in Table 3. This information indicates that as the drug product ages, the free base form is stable in the drug product.

Figure 13:
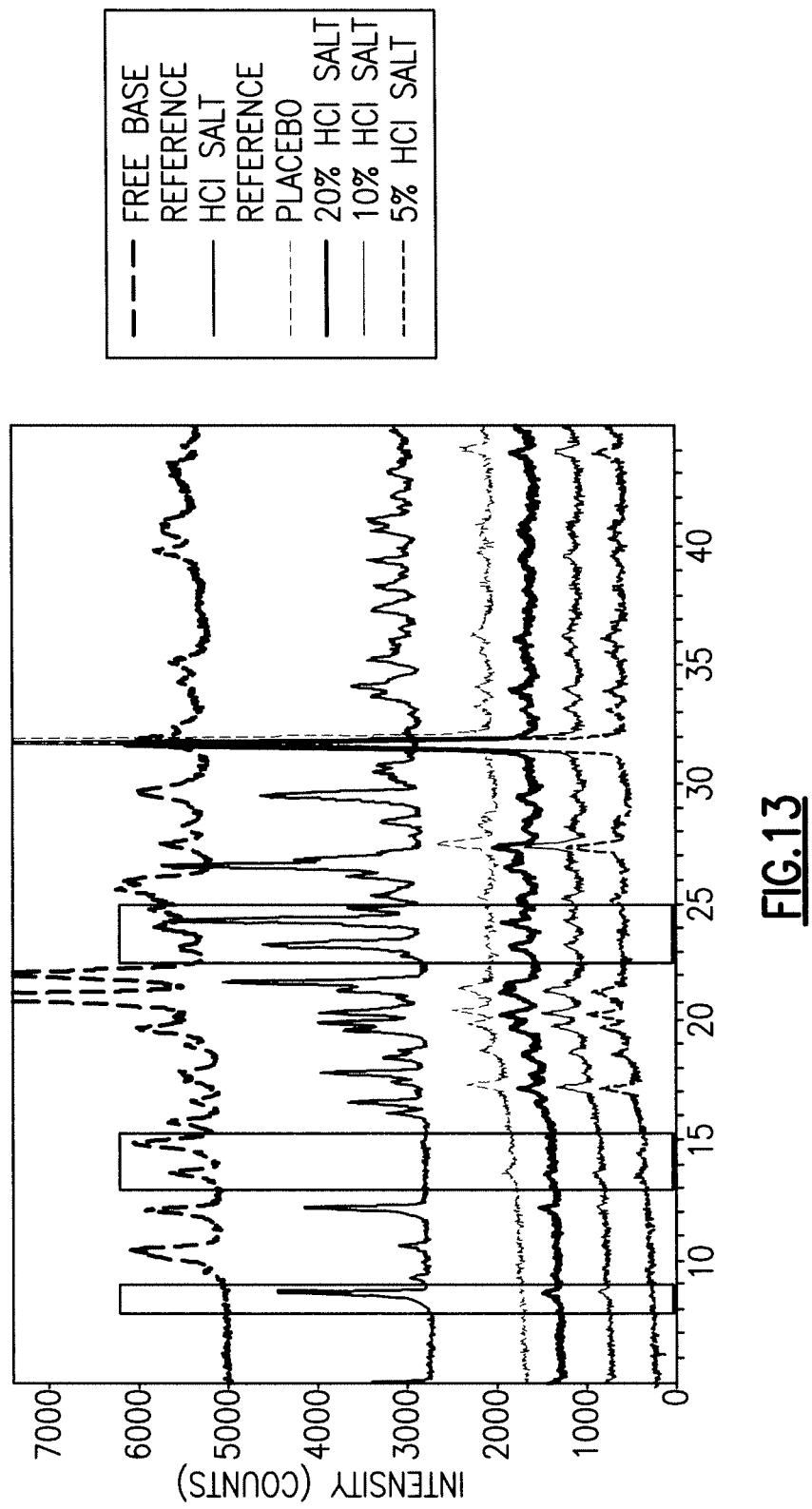
FIG. 13 shows an illustration of the sensitivity of X-ray powder diffraction analysis to detect besifloxacin HCl in ISV-403 drug product.
Figure 14:
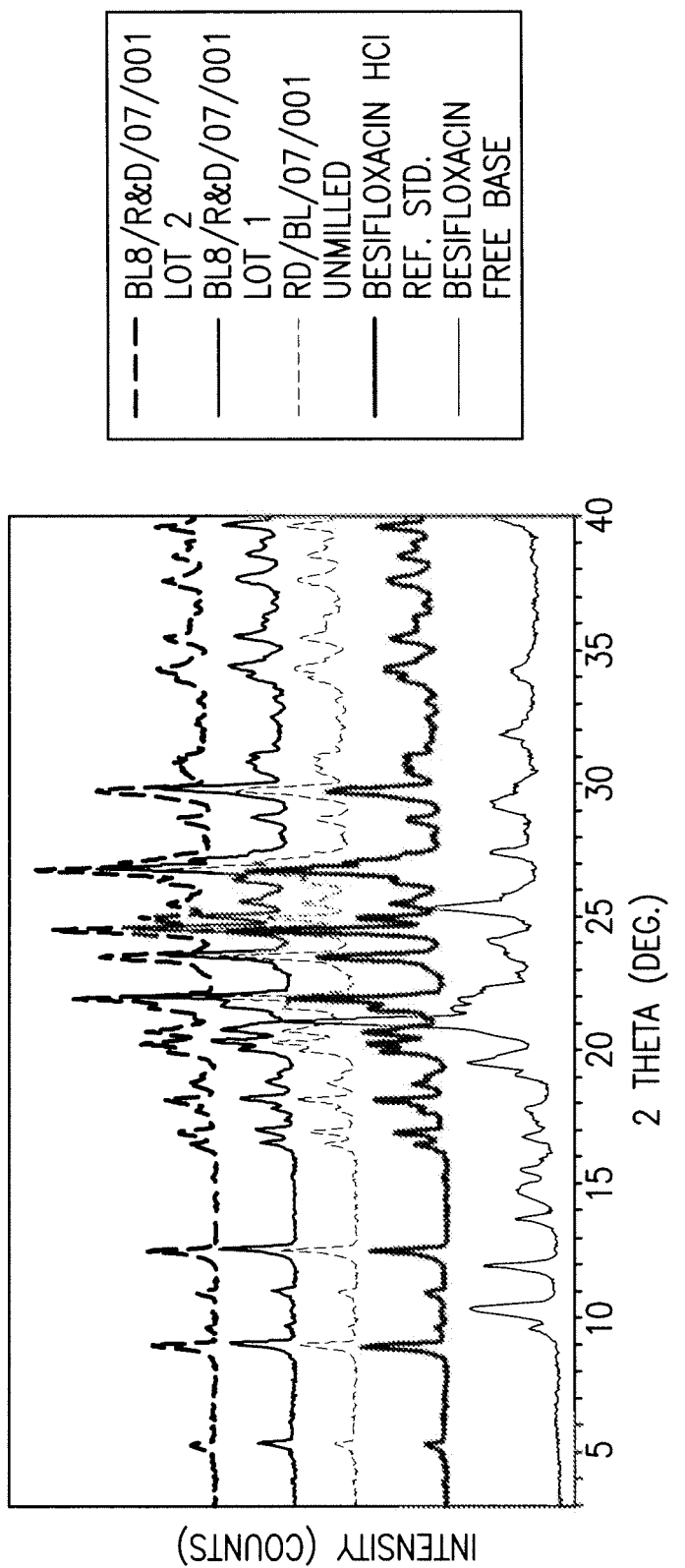
FIG. 14 shows the X-ray powder diffraction analysis patterns from 2-40 degrees 2Theta for second-laboratory manufactured besifloxacin HCl reference standard lot 14104J.

XRPD was demonstrated to detect between 5 and 10% w/w total besifloxacin HCl salt in the placebo as shown in FIG. 13.

Based on this sensitivity, no more than 25-50% of total besifloxacin could be present in the product as solid hydrochloride salt. It is unlikely that any solid HCl salt is present in the formulation at pH is 6.5, where the salt is soluble, but the solid free base has a solubility well below the nominal w/w concentration of the formulation. Rapid conversion of HCl salt to free base was observed in the pH solubility experiments at neutral to alkaline pH. Therefore, based on these XRPD analysis of product and the observed aqueous behavior of besifloxacin HCl salt at neutral pH, the free base is likely the predominant form of solid drug in the Besifloxacin Ophthalmic Suspension.

Conclusion

A crystalline form has been observed for besifloxacin HCl salt, the starting API form used to prepare Besifloxacin HCl Ophthalmic Suspension. The HCl salt was observed to dissolve and precipitate in a different crystalline form in aqueous media (pH >4). This new form was characterized as crystalline besifloxacin free base. Spectroscopic work indicates that solid besifloxacin free base contains zwitterionic besifloxacin as the fundamental molecular constituent. A unique XRPD pattern was identified for both the solid free base and HCl salt of besifloxacin. Although these forms had unique melting temperatures detected by DSC, melting appeared to result in rapid decomposition. There was no evidence from TGA for the existence of hydrated forms of besifloxacin free base.

Besifloxacin HCl salt was sparingly soluble in water, slightly soluble in methanol and ethanol and insoluble in acetonitrile and isopropanol. The compound had two ionizable functional groups, namely, a carboxylic acid and a primary amine. Due to the ionization states of these functional groups, a zwitterion predominates between pH 5.5-9.0, and the zwitterion is very slightly soluble (~0.1 mg/mL). At pH>9 and pH<5, the solubility of besifloxacin increased to maximum of ~10 mg/mL (pH 3) as a function of pH. By fitting the pH-solubility profile to the Henderson-Hasselbach equation, the intrinsic solubility of the zwitterion was determined to be 0.074 mg/mL, and the pKa of the carboxylic and primary amine groups were estimated as 5.65 and 9.91, respectively.

Based on XRPD analysis of drug product, the solid suspension particles were besifloxacin free base, and not besifloxacin HCl. This observation is consistent with solubility behavior in solution at pH 6.5 (product pH), where the free base of besifloxacin had a solubility of about 0.1 mg/mL in aqueous media, a value well below the nominal concentration of 6 mg/mL in Besifloxacin Ophthalmic Suspension. It appears that solid HCl salt converts to the free base form during suspension manufacture. These studies indicate that the solid free base of besifloxacin is the dominant drug phase in the Besifloxacin Ophthalmic Suspension (0.6%).

TABLE 1

Solubility of besifloxacin HCl salt (Lot 051157469) and Free base (Lot 2325-288) in various solvents at 22° C. ± 2° C.

| Solvent | HCl Salt Solubility** (mg/mL) | USP def | Free base Solubility** (mg/mL) | USP def |
|---|---|---|---|---|
| Water* | 10.635 | sparingly soluble | 0.079 | Insoluble |
| Methanol | 9.898 | slightly soluble | 0.135 | Very slightly soluble |
| Ethanol | 1.122 | slightly soluble | 0.033 | Insoluble |
| Acetonitrile | 0.012 | Insoluble | 0.005 | Insoluble |
| Isopropanol | 0.089 | Insoluble | 0.004 | Insoluble |

*A pH of 3.6 was observed for a saturated solution besifloxacin HCl salt in water and 8.1 for the free base form
**Solubility of free base

TABLE 2 pH-Dependence of Solubility of Besifloxacin HCl Salt (lot 050956330) Equilibrated in Water at 22° C. ± 2° C.

| pH | mg/mL |
|---|---|
| 3.54 | 10.63 |
| 3.58 | 10.19 |
| 3.72 | 10.29 |
| 3.95 | 4.18 |
| 4.58 | 0.71 |
| 4.87 | 0.59 |
| 5.15 | 0.24 |
| 5.17 | 0.27 |
| 5.43 | 0.22 |
| 5.95 | 0.12 |
| 6.31 | 0.10 |
| 6.45 | 0.10 |
| 6.49 | 0.08 |
| 6.72 | 0.08 |
| 8.14 | 0.08 |
| 9.11 | 0.08 |
| 9.59 | 0.10 |
| 9.63 | 0.10 |
| 10.37 | 0.27 |
| 10.85 | 0.85 |

TABLE 3

Age of the Besifloxican Ophthalmic Suspension (0.6%) When the Form of the Drug Substance in the Drug Product Was Tested

| Batch | Date of manufacture | Age (months) when analyzed by XRPD | Form identified in drug product* |
|---|---|---|---|
| D05Q | April 2004 | 25 | Free base |
| E04Q | May 2004 | 24 | Free base |
| E06Q | May 2004 | 24 | Free base |
| J04Q | September 2004 | 20 | Free base |
| Lot 965701 | December 2005 | 17 | Free base |

*XRPD patterns are shown in FIG. 12

Studies have been conducted to investigate whether besifloxacin HCl can exist in more than one crystalline form. A crystal form of the besifloxacin HCl and a crystal form of besifloxacin free base have been observed from crystal-form screening studies, the chemical process for manufacturing besifloxacin HCl and the manufacturing process for the besifloxacin drug product. These two crystal-forms were found to have unique x-ray diffraction patterns as can be seen in FIG. 9.

Micronized besifloxacin HCl is used as a starting material for drug product manufacturing. During the manufacturing process the HCl salt is converted to besifloxacin free base. In solution at the product pH of approximately 6.5, the besifloxacin free base is the favored form. Powder x-ray diffraction results from testing of dried drug product reveals a lack of diffraction peaks for the HCl salt and the presence of diffraction peaks characteristic of the free base.

Experimental Samples

| Manufacturer Lot (#) | Material | Manufacturer or Comments |
|---|---|---|
| R&D/BL/07/001 | Besifloxacin HCl Unmilled | First laboratory |
| BL8/R&D/07/001 Lot 1 | Besifloxacin HCl Micronized | First laboratory |
| BL8/R&D/07/001 Lot 2 | Besifloxacin HCl Micronized | First laboratory |
| 2325-293 | Besifloxacin Free Base Unmilled | Third laboratory |
| 14104J | Besifloxacin HCl Micronized Reference Standard | Second laboratory |
| 01085J | Besifloxacin HCl Micronized | Second laboratory |
| 03063J | Besifloxacin HCl Micronized | Second laboratory |
| 05126J | Besifloxacin HCl Micronized | Second laboratory |
| 30095J | Besifloxacin HCl Micronized | Second laboratory |
| Batch #10 | Besifloxacin HCl Unmilled | Second laboratory |
| 5% Free Base Added to Neuland Lot 2 | Lot 2325-293 and BL8/R&D/07/001 Lot 2 | Spiking Study 1 Sample |
| 7.5% Free Base Added to Neuland Lot 2 | Lot 2325-293 and BL8/R&D/07/001 Lot 2 | Spiking Study 1 Sample |
| 11% Free Base Added to Neuland Lot 2 | Lot 2325-293 and BL8/R&D/07/001 Lot 2 | Spiking Study 1 Sample |
| 14% Free Base Added to Neuland Lot 2 | Lot 2325-293 and BL8/R&D/07/001 Lot 2 | Spiking Study 1 Sample |
| 17% Free Base Added to Neuland Lot 2 | Lot 2325-293 and BL8/R&D/07/001 Lot 2 | Spiking Study 1 Sample |
| 5% Free Base Added to B&L Reference Std. | Lot 2325-293 and Lot 14104J | Spiking Study 2 Sample |
| 10% Free Base Added to B&L Reference Std. | Lot 2325-293 and Lot 14104J | Spiking Study 2 Sample |

The besifloxacin HCl and free base samples were lightly ground with an agate mortar and pestle to ensure a similar API particle size for each sample and to avoid preferred orientation. The sample powder was placed near the center of the sample well in a rectangular "zero background" sample holder. In an effort to achieve a flat powder bed of the appropriate height the powder was spread across the center of the well then compressed in a downward motion with a glass slide covered with weigh paper Powder X-Ray Diffraction Powder x-ray diffraction patterns were collected using a Rigaku MiniFlex desktop x-ray diffractometer (serial #CD016610). The MiniFlex has a vertical-oriented goniometer (150 mm radius) and a Copper sealed x-ray tube operated at 30 kV/15 mA with a 6° take-off angle. The instrument uses a variable (theta compensating) divergence slit system and a Nickel Kβ filter. A scintillation counter is used as the detector. Jade version 7.5 software from Materials Data, Inc. was used for pattern evaluation and generation of figures.

Samples were scanned over a region of 2-40° 2θ at 1.5° degree/minute with a with a step size of 0.05°/step or 7-23° 2θ at 0.5° degree/minute with a with a step size of 0.03°/step. A qualitative determination of physical-form for the Neuland manufactured lots was carried out by comparison of each lot's diffraction pattern with that of the besifloxacin HCl reference standard and besifloxacin free base.

System suitability was verified for the MiniFlex x-ray diffractometer by daily measurement of a silicon standard over a range of 28-29° 2θ at 1.0° degree/minute with a with a step size of 0.02°/step. System suitability was achieved when the summit of the d111 diffraction for the silicon standard was measured as 28.44±0.02° 2θ.

Sample Preparation

The besifloxacin HCl and free base samples were lightly ground with an agate mortar and pestle to ensure a similar API particle size for each sample and to avoid preferred orientation. The sample powder was placed near the center of the sample well in a rectangular "zero background" sample holder. In an effort to achieve a flat powder bed of the appropriate height the powder was spread across the center of the well then compressed in a downward motion with a glass slide covered with weigh paper.

Results

X-ray diffraction patterns for First-laboratory manufactured besifloxacin HCl, Second-laboratory manufactured besifloxacin HCl reference standard and a Bausch & Lomb manufactured besifloxacin free base are shown in FIGS. 14 and 26-29. The major diffraction peaks in First-laboratory lots R&D/BL/07/001, BL8/R&D/07/001 Lot 1 and BL8/R&D/07/001 Lot 2 are a match to those in the Bausch & Lomb besifloxacin HCl reference standard (lot 14104J) confirming the First-laboratory lots are the same crystal-form as the besifloxacin HCl reference standard. The x-ray diffraction patterns for the First-laboratory manufactured lots are also a good match with the patterns for all of the other besifloxacin HCl lots sourced from the Second laboratory (FIGS. 15 and 30-33).

Figure 15:
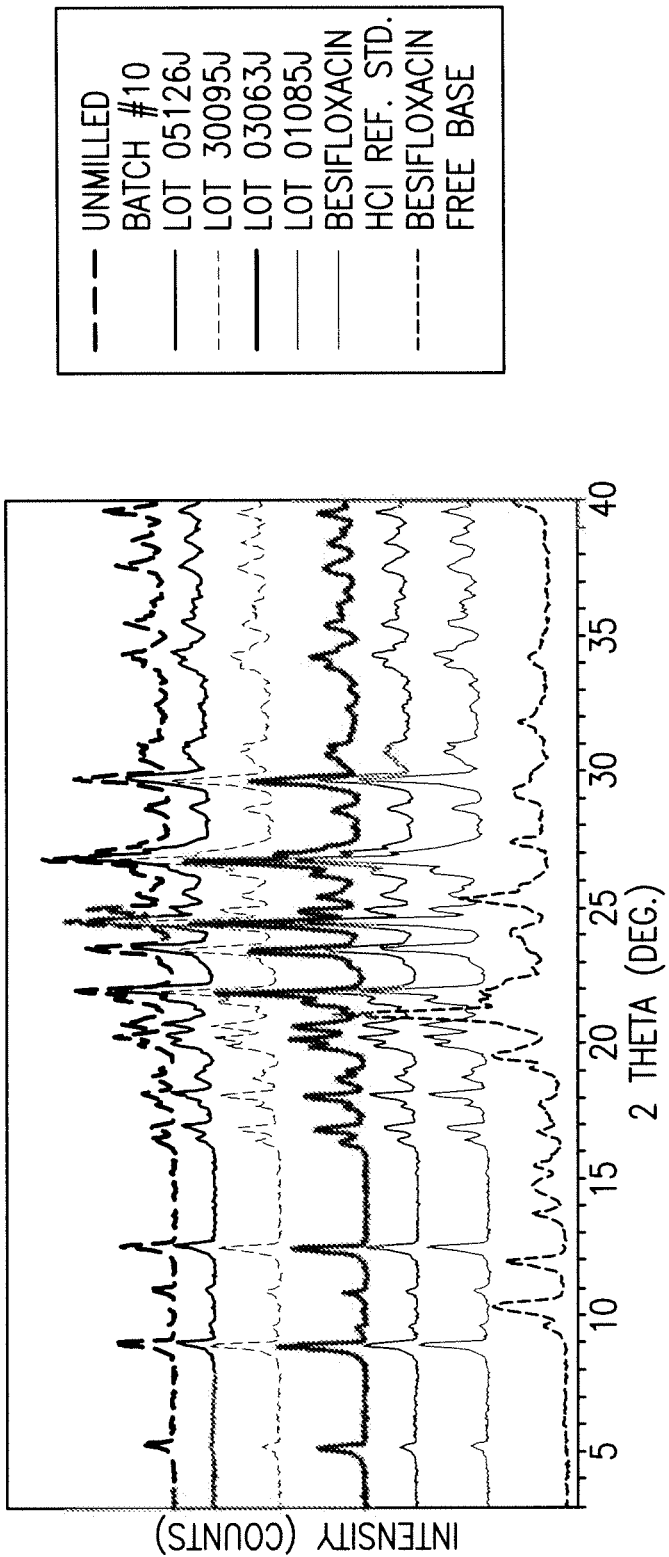
FIG. 15 shows X-ray powder diffraction analysis patterns from 3-40 degrees 2Theta for second-laboratory manufactured besifloxacin HCl and Bausch & Lomb manufactured besifloxacin free base.
Figure 16:
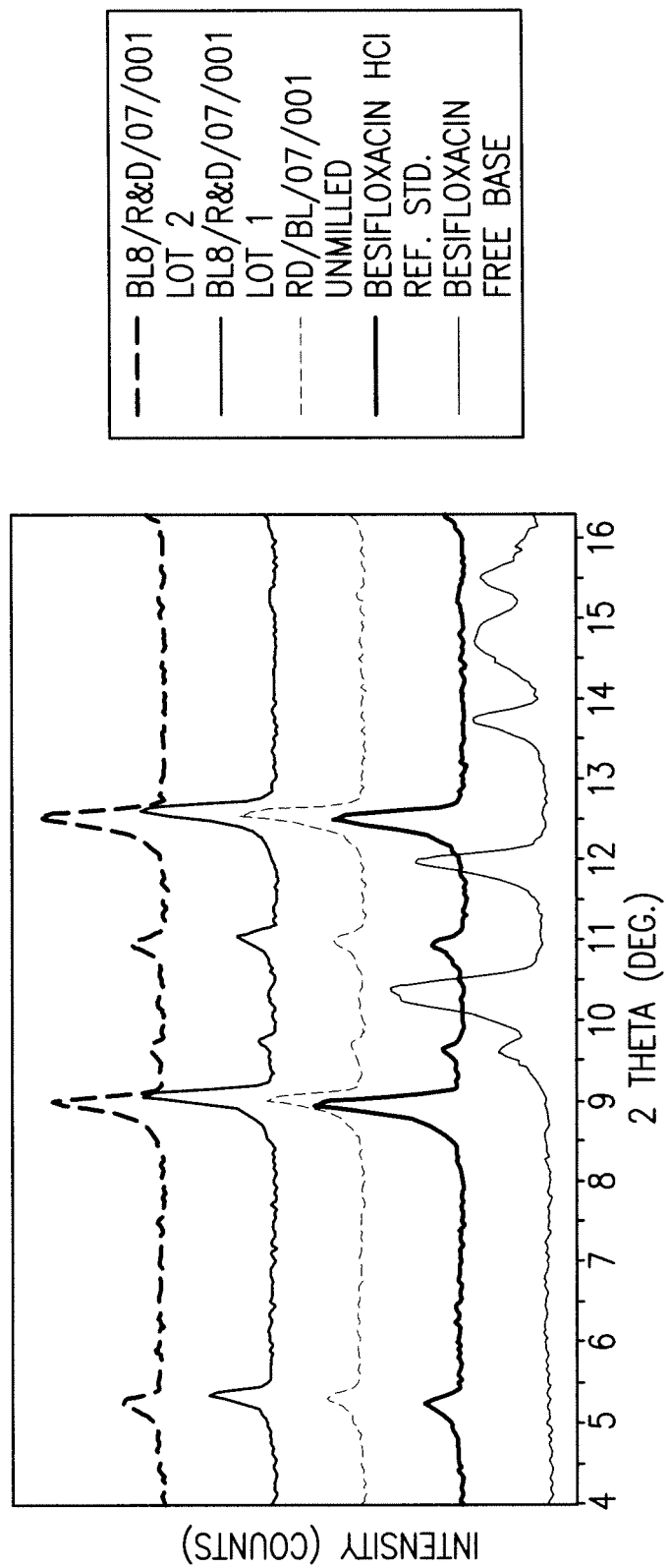
FIG. 16 shows the X-ray powder diffraction analysis patterns from 4-16 degrees 2Theta for first-laboratory manufactured besifloxacin HCl lots, the second-laboratory manufactured besifloxacin HCl reference standard and Bausch & Lomb manufactured besifloxacin free base.
Figure 17:
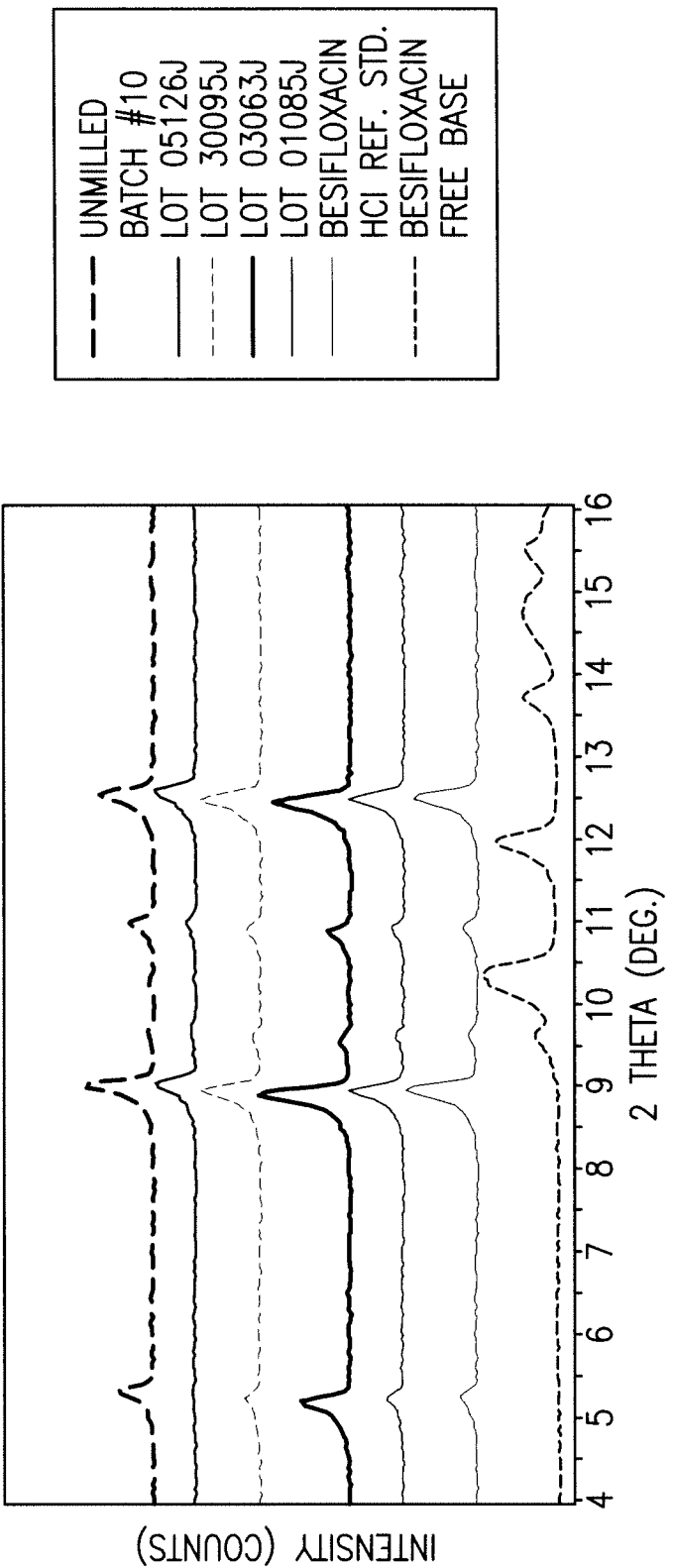
FIG. 17 shows the X-ray powder diffraction analysis patterns from 4-16 degrees 2Theta for second-laboratory manufactured besifloxacin HCl lots and Bausch & Lomb manufactured besifloxacin free base.
Figure 18:
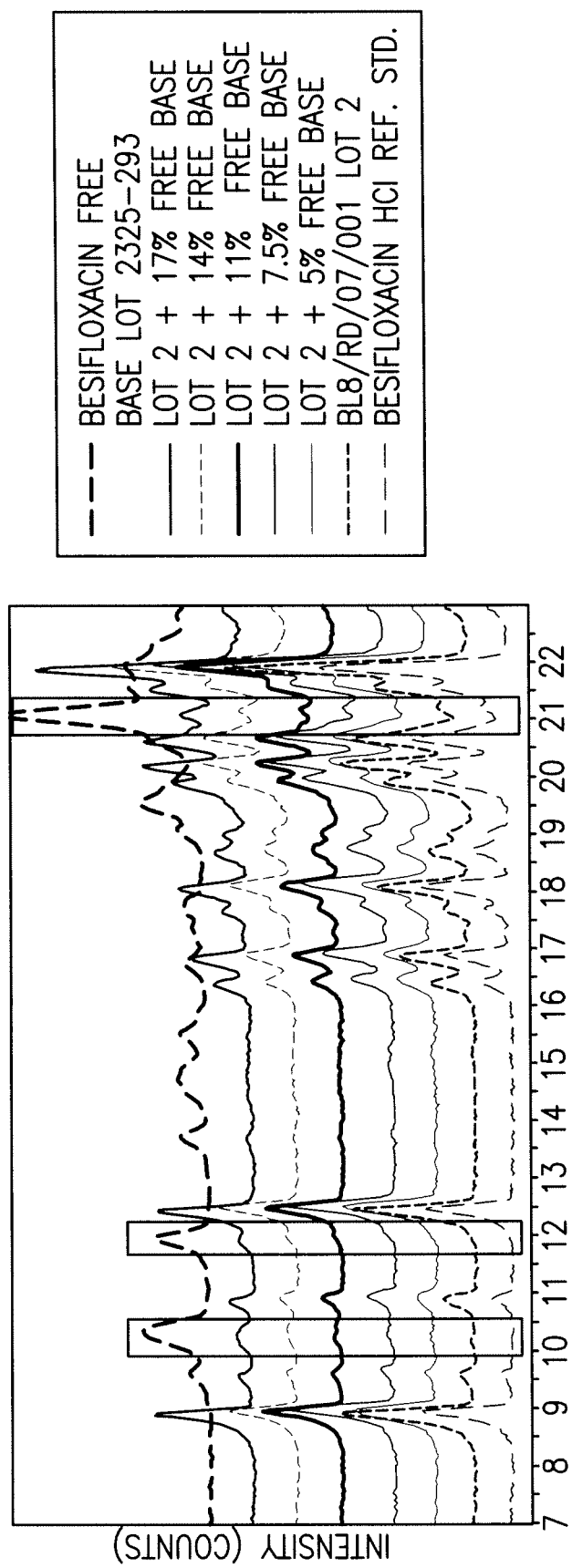
FIG. 18 shows the X-ray powder diffraction analysis patterns for spiking study samples where besifloxacin free base Lot 2325-293 was spiked into first-laboratory manufactured besifloxacin HCl BL8/R&D/07/001 Lot 2 to define peaks indicating increasing free base content.
Figure 19:
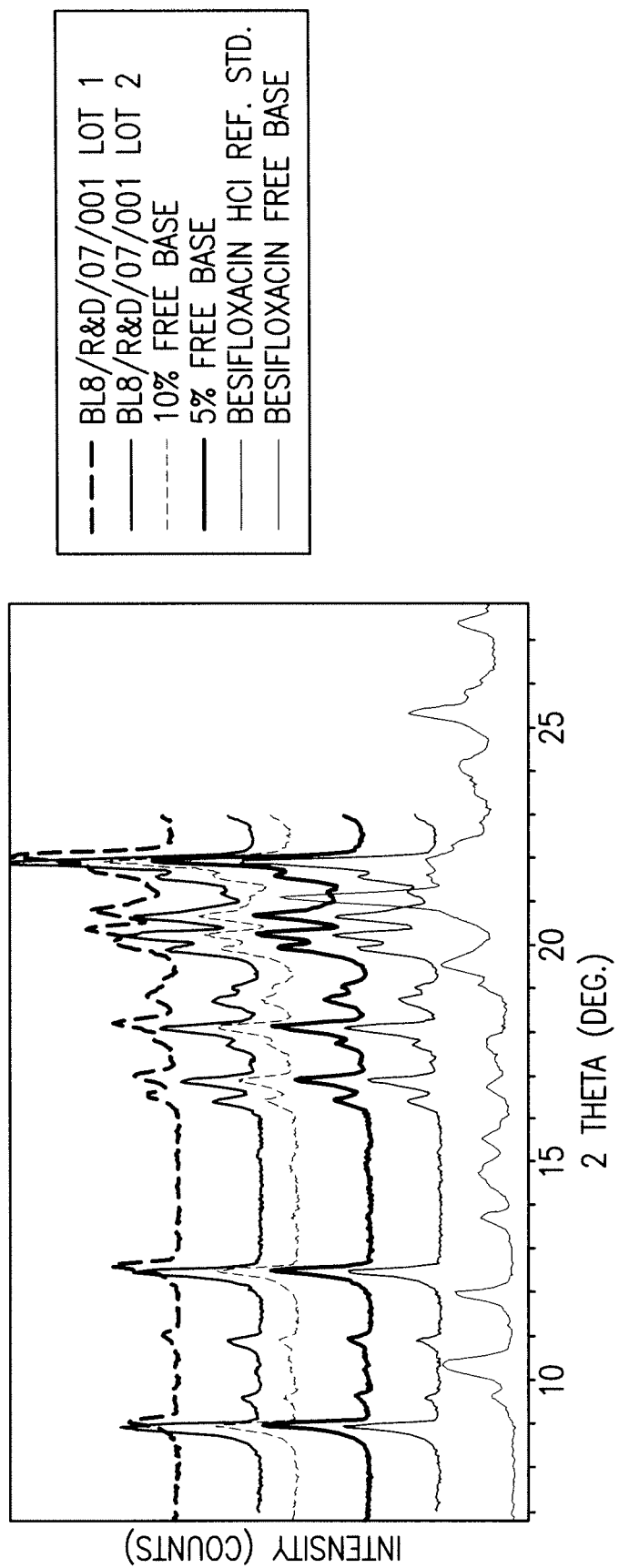
FIG. 19 shows the X-ray powder diffraction analysis patterns for spiking study samples where besifloxacin free base Lot 2325-293 was spiked into the second-laboratory manufactured besifloxacin HCl reference standard.
Figure 20:
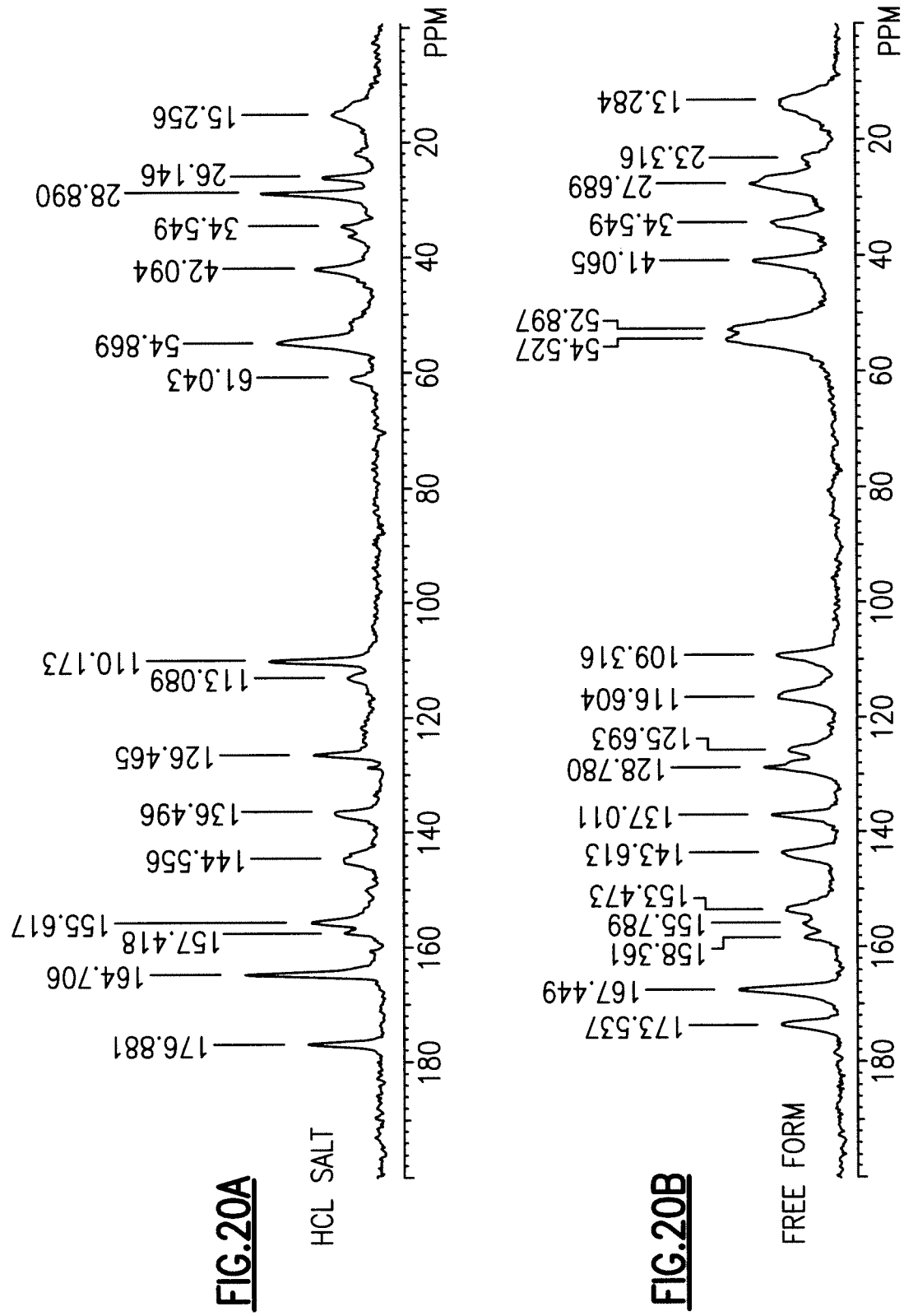
FIG. 20A shows the $^{13}$C NMR spectrum of besifloxacin HCl salt
FIG. 20B shows the $^{13}$C NMR spectrum of besifloxacin free base.
Figure 21:
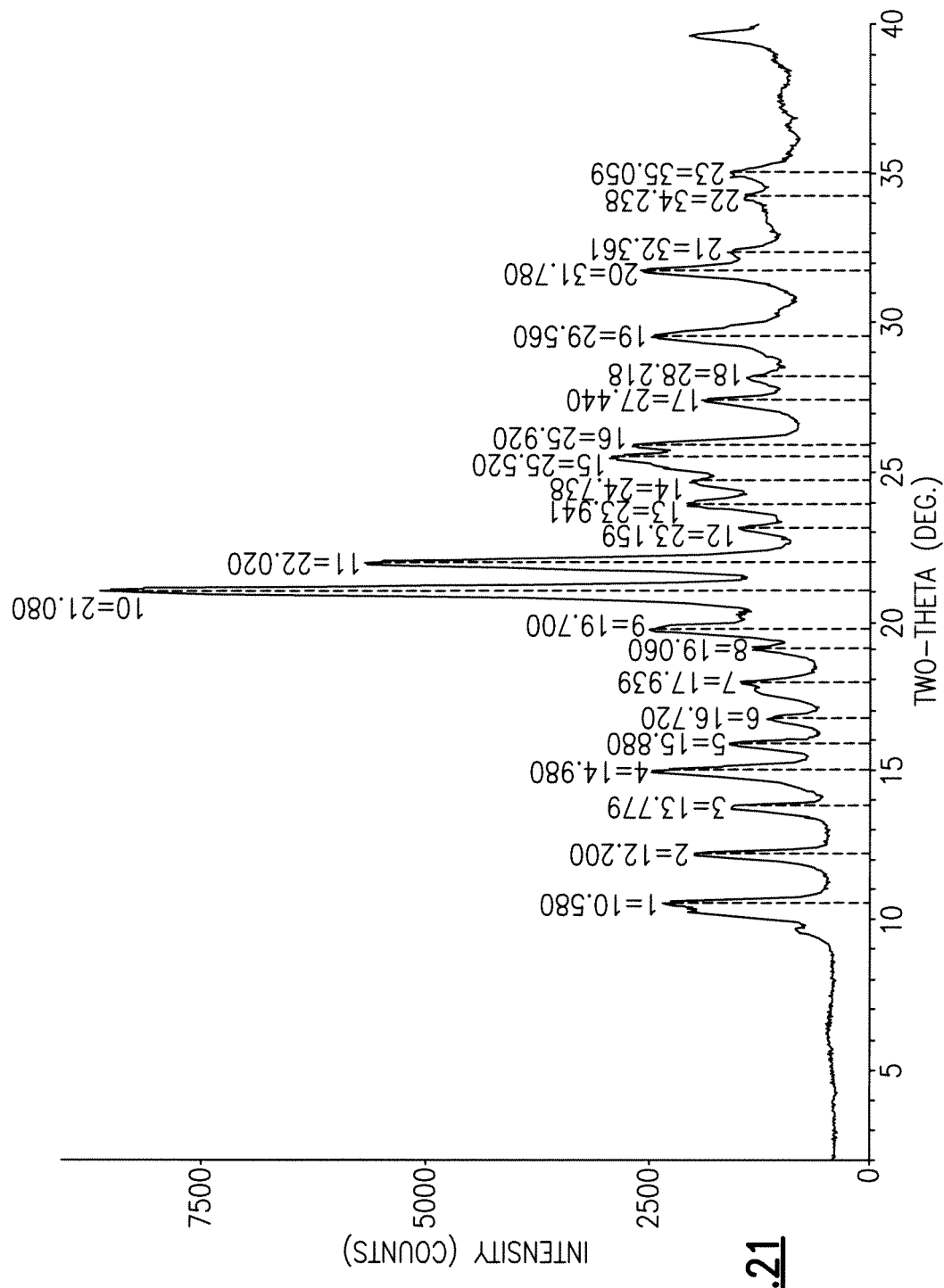
FIG. 21 shows the average X-ray powder diffraction analysis pattern of three lots of besifloxacin free base.
Figure 23:
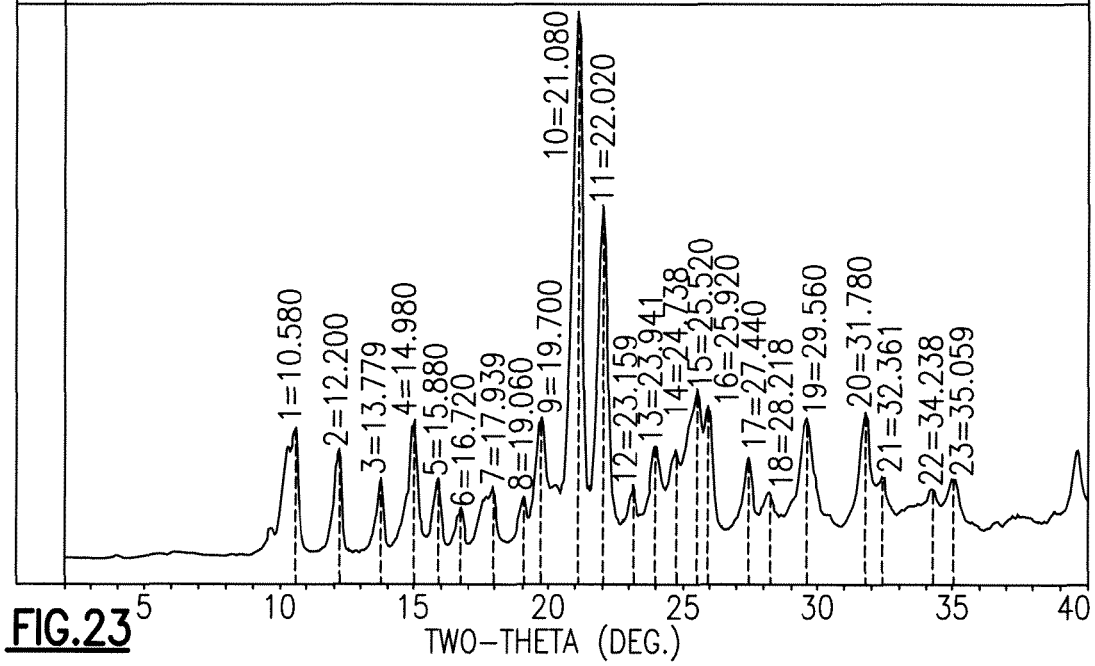
FIG. 23 shows the X-ray powder diffraction analysis peak table for besifloxacin free base, Lot 2325-293.
Figure 24:
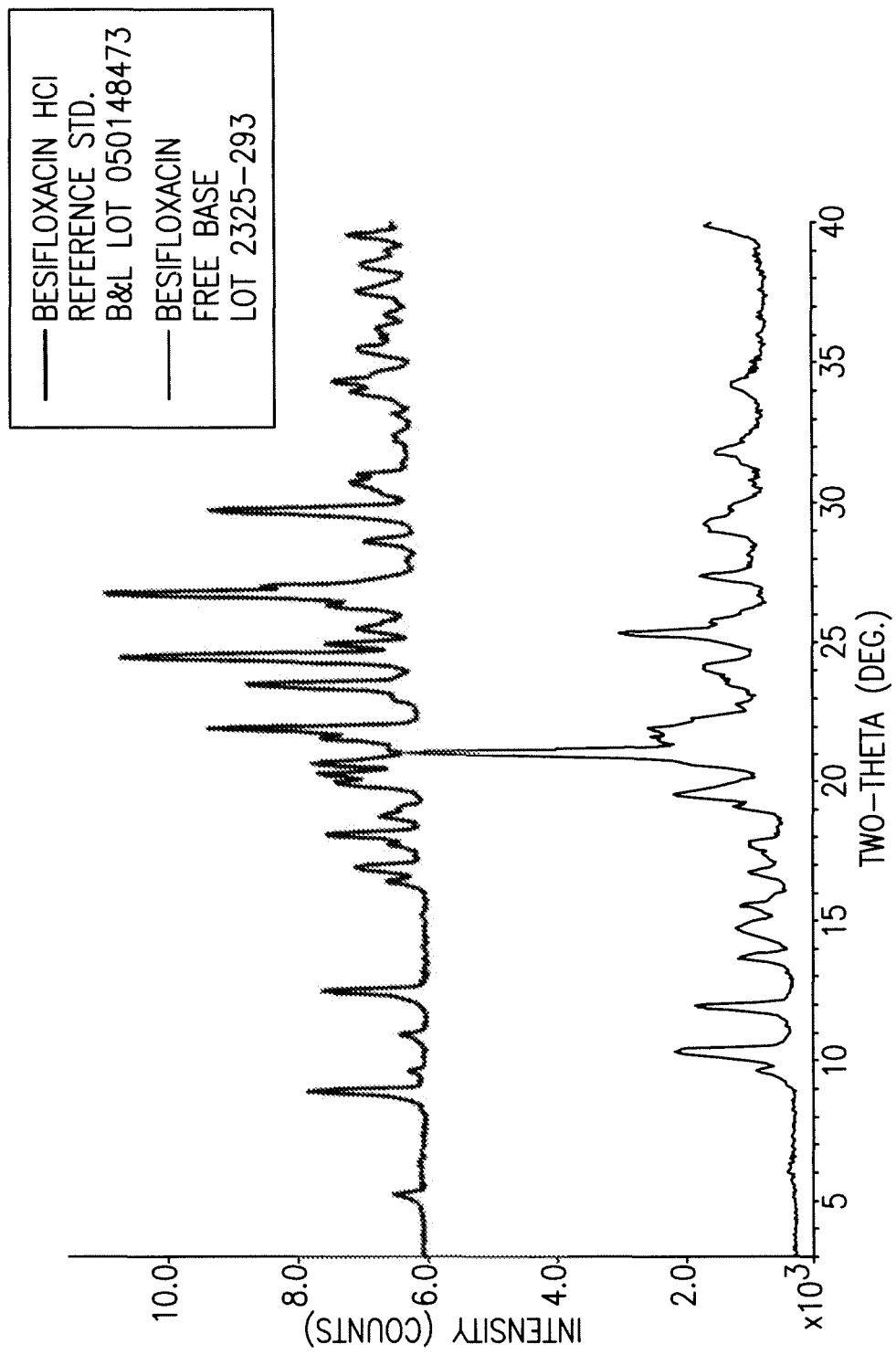
FIG. 24 shows the comparison of X-ray powder diffraction analysis patterns of besifloxacin HCl reference standard and besifloxacin free base Lot 2325-293.
Figure 26:
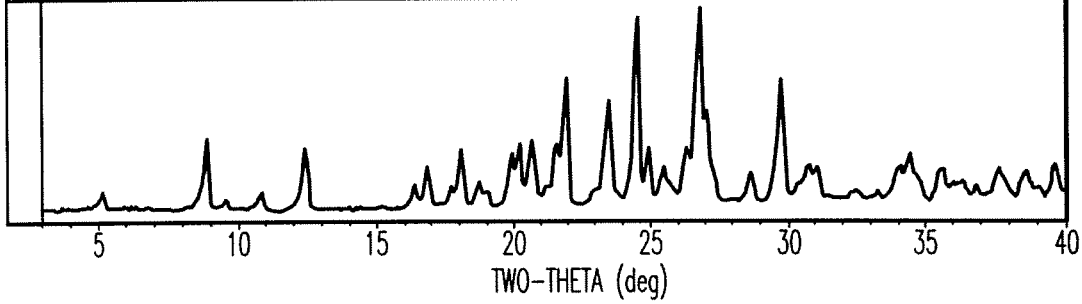
FIG. 26 is an X-ray Diffraction Peak Report for Micronized Besifloxacin HCl Reference Standard (B&L lot 050148473 and Second laboratory lot 14104J).
Figure 27:
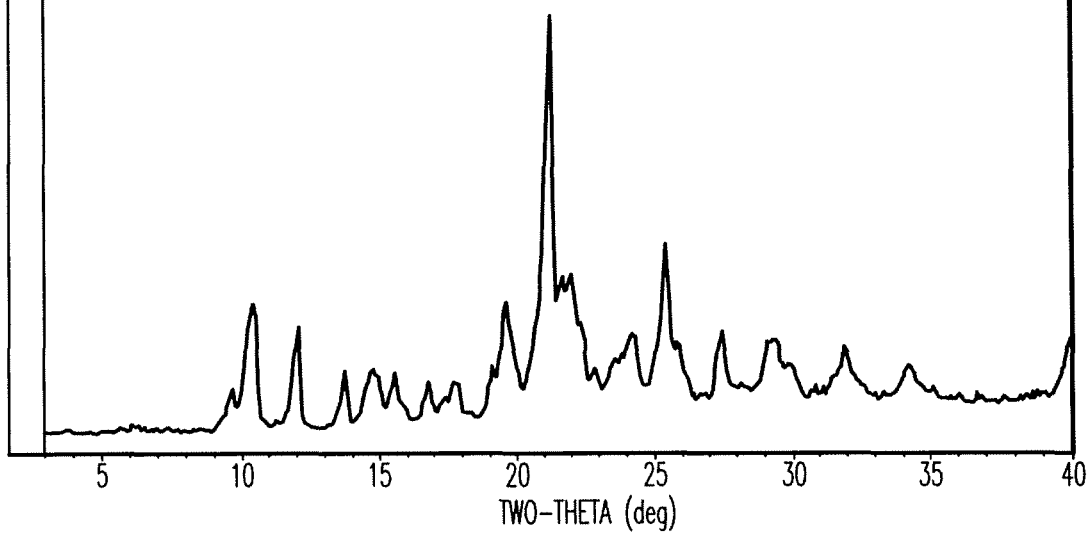
FIG. 27 is an X-ray Diffraction Peak Report for Besifloxacin Free Base (B&L 2325-293).
Figure 28:
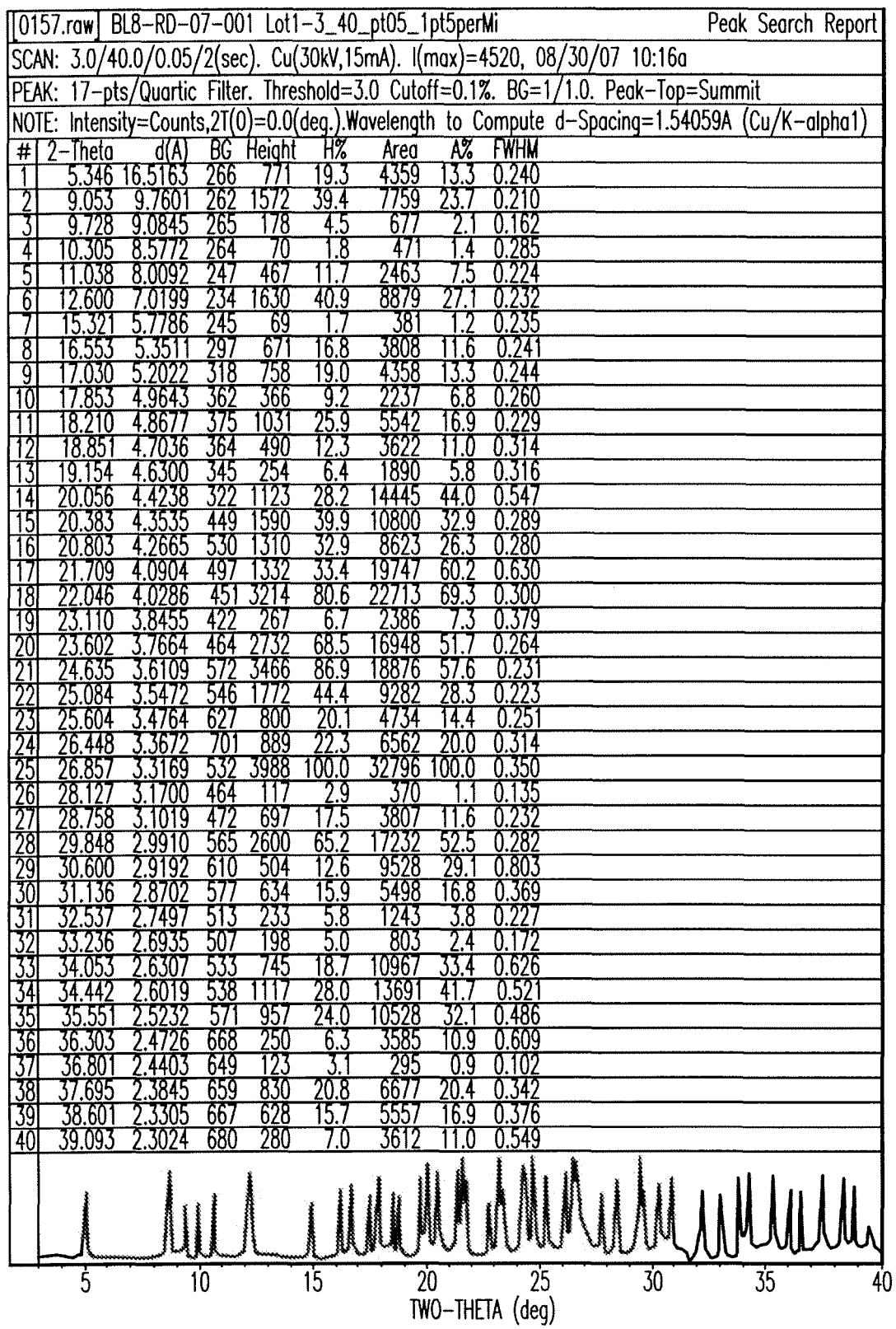
FIG. 28 is an X-ray Diffraction Peak Report for Micronized Besifloxacin HCl (B&L lot 070876736 and First laboratory lot BL8/R&D/07/001 Lot I).
Figure 29:
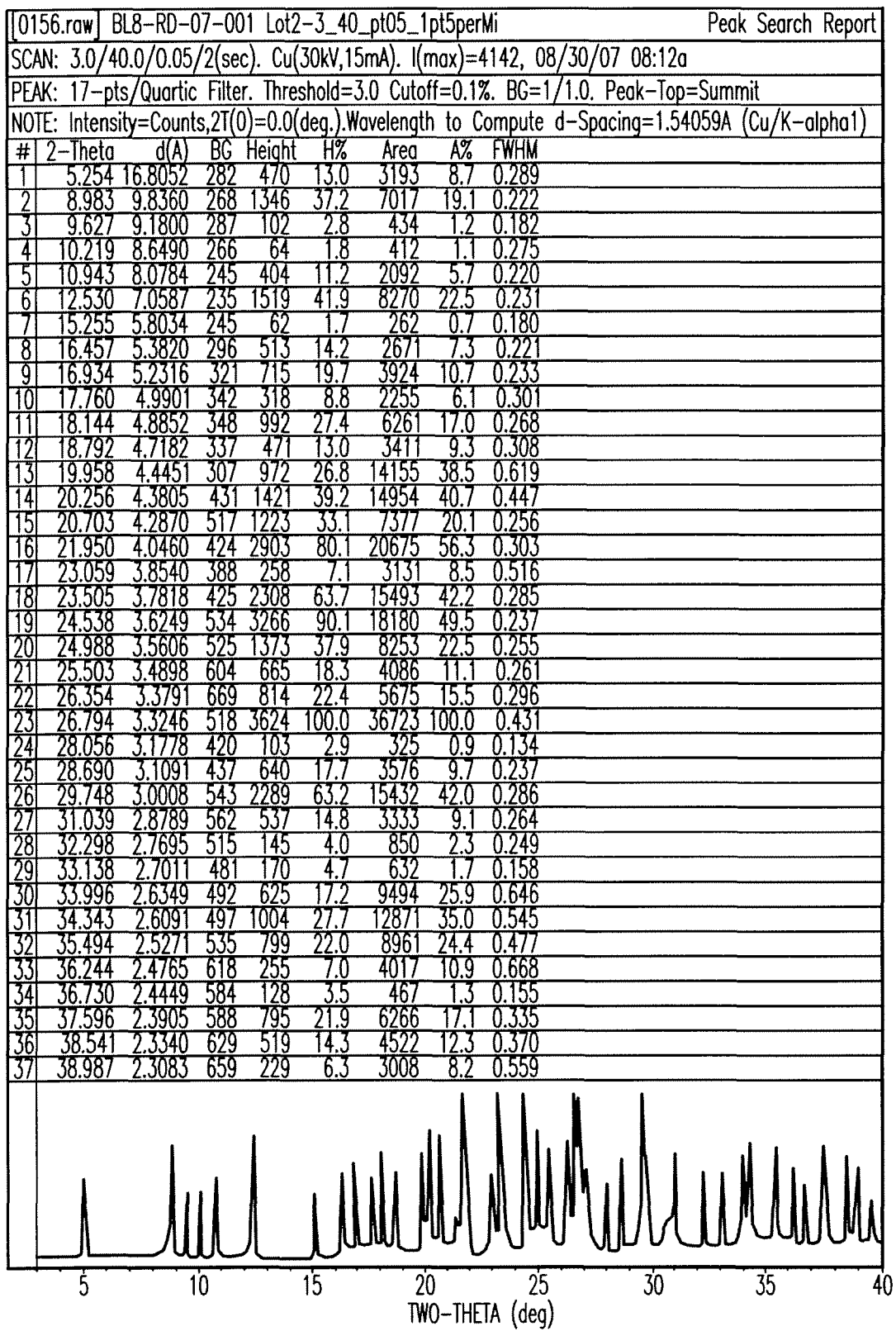
FIG. 29 is an X-ray Diffraction Peak Report for Micronized Besifloxacin HCl (B&L lot 070876768 and First-laboratory lot BL8/R&D/07/001 Lot II).
Figure 30:
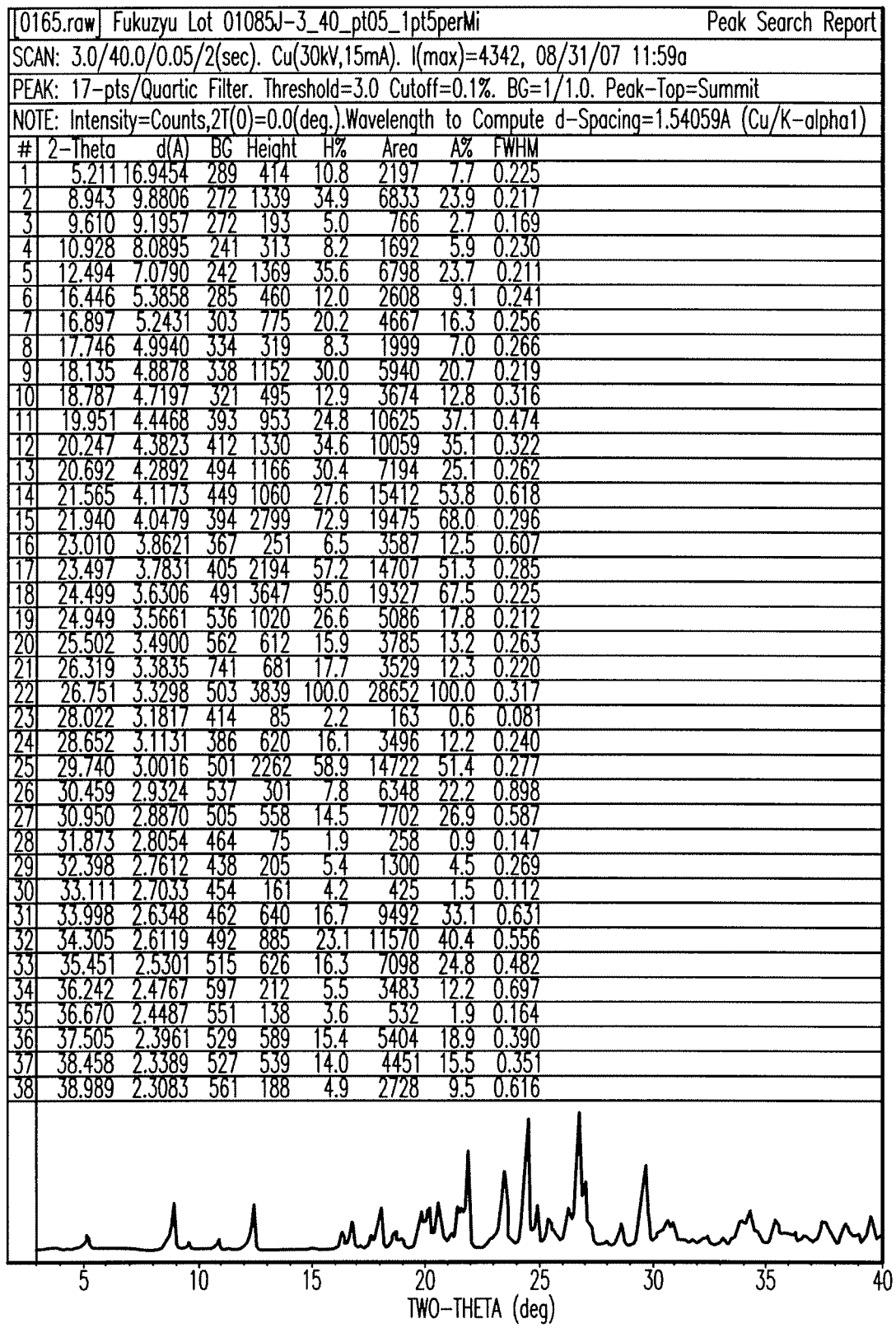
FIG. 30 is an X-ray Diffraction Peak Report for Micronized Besifloxacin HCl (B&L lot 050956330 and Second-laboratory lot 01085J).
Figure 31:
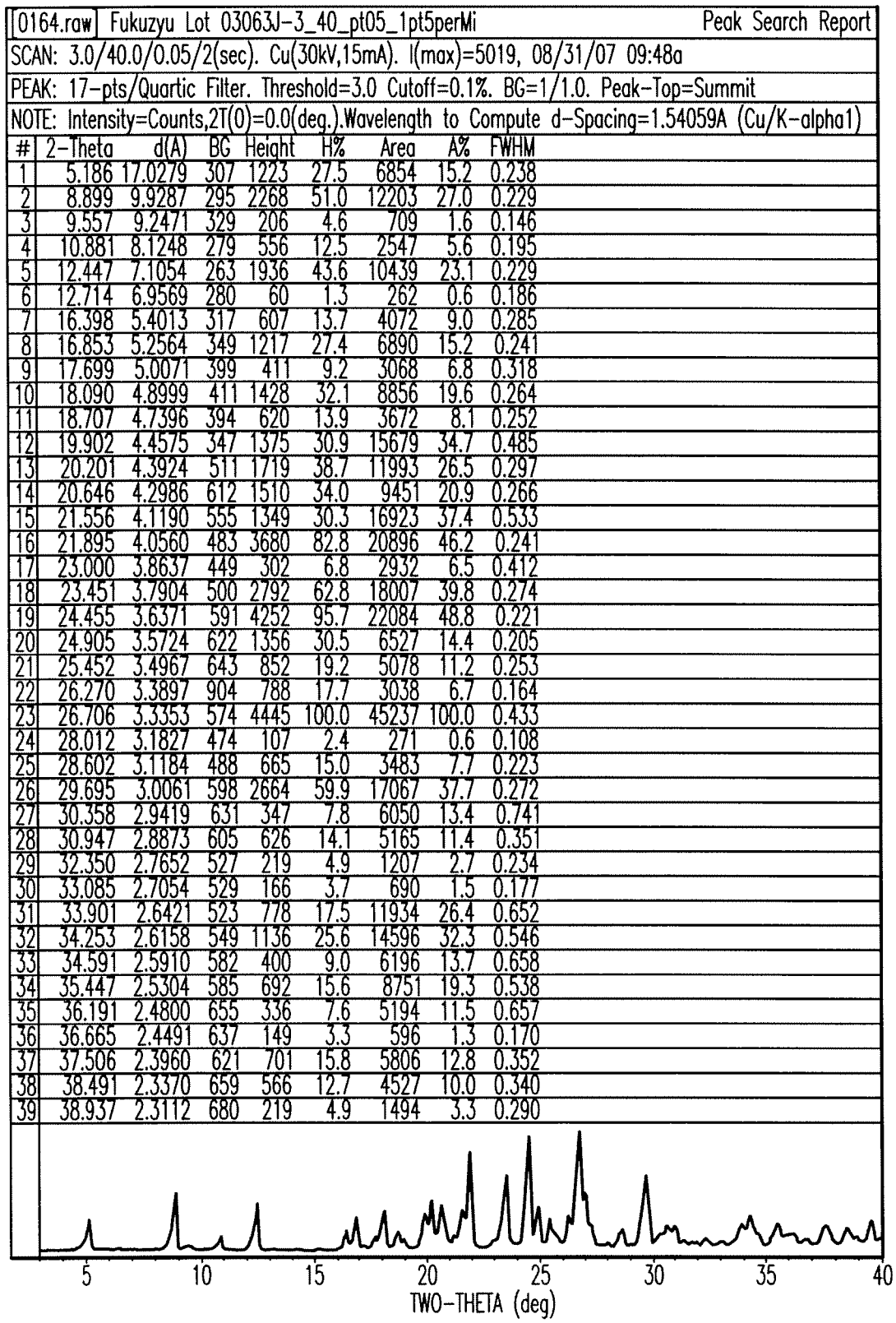
FIG. 31 is an X-ray Diffraction Peak Report for Micronized Besifloxacin HCl (Second-laboratory lot 03063J).
Figure 32:
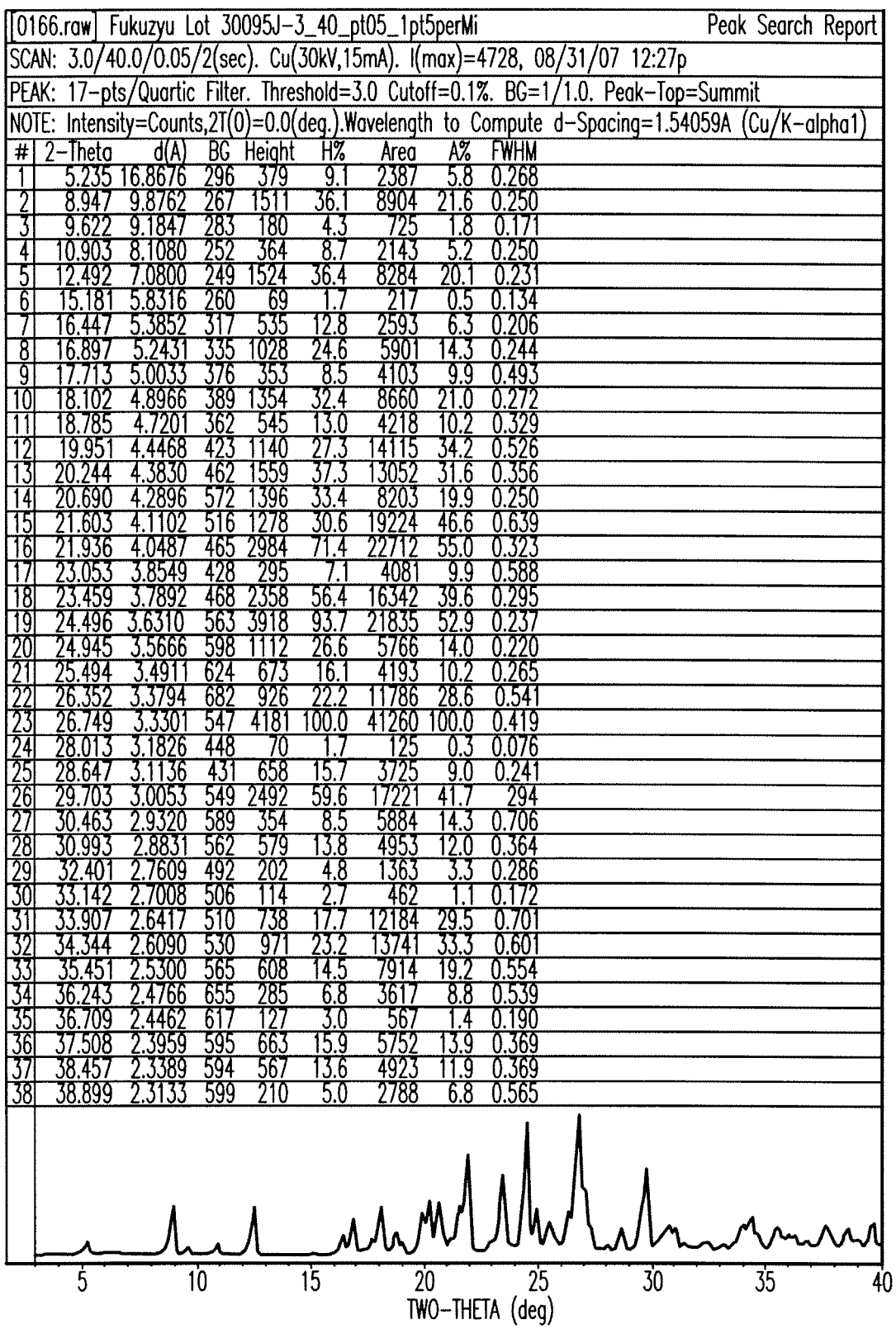
FIG. 32 is an X-ray Diffraction Peak Report for Micronized Besifloxacin HCl (B&L lot 051157469 and Second-laboratory lot 30095J).
Figure 33:
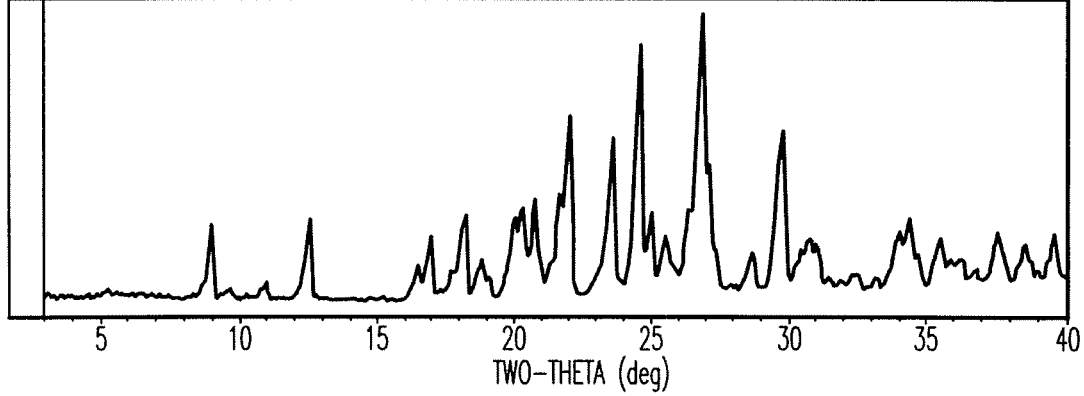
FIG. 33 is an X-ray Diffraction Peak Report for Micronized Besifloxacin HCl (Second-laboratory lot 05126J).

A small difference in the x-ray diffraction patterns for the three First-laboratory lots as compared to that of the besifloxacin HCl reference standard was observed as a very minor peak at about 10.3° 2θ (FIG. 16). This minor diffraction peak appears to also be present in some Second-laboratory manufactured lots (FIGS. 15 and 17). Besifloxacin free base was spiked into a sample of First-laboratory manufactured besifloxacin HCl (BL8/R&D/07/001 Lot 2) to determine whether the diffraction peak at 10.3° 2θ would increase in intensity as the free base content of the powder rose. FIG. 18 shows the x-ray diffraction patterns for the samples from this first spiking study. Increasing levels of besifloxacin free base in the spiking study samples resulted an increase in the intensity of the diffraction peaks at 10.3° (d=8.6), 12.0° (d=7.4) and 21.2° 2θ (d=21.2). Therefore, the minor diffraction peak at 10.3° 2θ is confirmed as an indicator of the presence of besifloxacin free base. A second spiking study was conducted with besifloxacin free base spiked into the besifloxacin HCl reference standard. FIG. 19 provides the x-ray diffraction patterns for the second spiking study samples. The "as is" besifloxacin reference standard exhibits no detectable diffraction peak at 10.3° 2θ. After as little as 5% of the besifloxacin free base is added to the besifloxacin HCl reference standard the minor peak at 10.3° 2θ can be detected. Using only two spiking levels (5% and 10% free base) from the second study and assuming that the besifloxacin HCl reference standard and the besifloxacin free base are pure, a rough estimate of the amount of free base in the three First-laboratory lots was made. Table 4 summaries the second spiking study results and provides rough estimates of the free base content in the First-laboratory micronized besifloxacin HCl lots. Using the peak height for the diffraction peak at 10.2-10.3° 2θ it is estimated that First-laboratory manufactured micronized lots BL8/R&D/07/001 Lot 1 and BL8/R&D/07/001 Lot 2 contain between 5-9% besifloxacin free base. Among the Second-laboratory manufactured lots, only unmilled batch #10 contained detectable free base. However, Second-laboratory micronized lots 05126J, 03063J and 01085J all exhibit a minor baseline blip in the area of 10.3° 2θ which likely indicates that these lots contain some besifloxacin free base but probably ≦5%.

TABLE 4

Results from Studies Spiking Study #2:
Free Base Spiked into Besifloxacin HCl

| Study or Sample ID | Free Base Added (% wt) | Peak Height (counts) | Rough Estimate of Free Base from Linear Fit [Free Base = Peak Ht./1606.4 * 100] (Estimated % Wt Free Base) |
|---|---|---|---|
| Spiking Study #2 | 0.0 | 0 | 0 |
| Free Base Spiked into | 5.0 | 118 | 7 |
| Besifloxacin HCl | 9.9 | 140 | 9 |
| Reference Standard | | | |
| BL8/R&D/07/001 Lot I | NA | 81 | 5 |
| BL8/R&D/07/001 Lot II | NA | 144 | 9 |

NA = not applicable

In another aspect, the present invention provides a pharmaceutical composition comprising a molecular crystal of besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid) characterized by an X-ray powder diffraction ("XRPD") spectrum that comprises peaks at 2θ angles of 10.6, 15, 19.7, 21.1, and 22°±0.2°.

In yet another aspect, the present invention provides a pharmaceutical composition comprising a molecular crystal of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by a DSC (differential scanning calorimetry) melting peak at 288° C.

In a further aspect, the present invention provides a pharmaceutical composition comprising a molecular crystal of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by $^{13}$C NMR spectrum having peaks at 23.3, 27.7, 41.1, 54.5, 116.6, and 153.5 ppm.

In still another aspect, the present invention provides a pharmaceutical composition comprising a molecular crystal of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by pKa values of 5.65 and 9.91.

In yet another aspect, the present invention provides a pharmaceutical composition comprising a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°; or by a DSC melting peak at 288° C.; or by a $^{13}$C NMR spectrum having peaks at 23.3, 27.7, 41.1, 54.5, 116.6, and 153.5 ppm; or by pKa values of 5.65 and 9.91.

In a further aspect, the present invention provides a pharmaceutical composition comprising a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxo-quinoline-3-carboxylic acid characterized by an X-ray powder diffraction ("XRPD") spectrum that comprises peaks at 2θ angles of 10.6, 15, 19.7, 21.1, and 22°±0.2°; a DSC melting peak at 288° C.; and a $^{13}$C NMR spectrum having peaks at 23.3, 27.7, 41.1, 54.5, 116.6, and 153.5 ppm.

In still another aspect, the present invention provides a pharmaceutical composition comprising a molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°; a DSC melting peak at 288; a $^{13}$C NMR spectrum having peaks at 23.3, 27.7, 41.1, 54.5, 116.6, and 153.5 ppm; and pKa values of 5.65 and 9.91.

A pharmaceutical composition of the present invention can be used to treat infection, such as bacterial infection, by administering such a composition to a subject.

Such a pharmaceutical composition may be adapted for administration by appropriate routes, for example by the oral (including buccal or sublingual), rectal, nasal, topical (including buccal, sublingual or transdermal), vaginal or parenteral (including subcutaneous, intramuscular, intravenous or intradermal) route. Such compositions may be prepared by any method known in the art of pharmacy, for example by bringing into association besifloxacin (or a salt or an ester thereof) with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical compositions adapted for topical administration may be formulated as ointments, creams, suspensions, lotions, powders, solutions, pastes, gels, sprays, aerosols or oils.

For treatments of the eye or other external tissues, for example skin, the compositions may be applied as a topical solution, suspension, emulsion, dispersion, ointment, or cream, as appropriate. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Pharmaceutical compositions adapted for nasal administration wherein the carrier is a solid include a coarse powder having a particle size for example in the range 10 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators.

Pharmaceutical compositions adapted for vaginal administration may be presented as pessaries, tampons, creams, gels, pastes, foams or spray compositions.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous Injection solutions and suspensions may be prepared from sterile powders, granules and tablets.

Preferred unit dosage compositions are those containing a daily dose or sub-dose, as herein above recited, or an appropriate fraction thereof, of an active ingredient.

In one embodiment, such a pharmaceutical composition comprises an aqueous carrier.

In another embodiment, such a pharmaceutical composition comprises an organic carrier, such as a hydrophobic or a hydrophilic organic material.

A suitable concentration is in the range from about 0.001 to about 10 percent (or alternatively, from about 0.01 to about 5 percent, or from about 0.01 to about 2 percent, or from about 0.01 to about 1 percent, or from about 0.001 to about 1 percent, or from about 0.05 to about 1 percent, or from about 0.05 to about 2 percent, or from about 0.1 to about 0.5 percent, from about 0.5 to about 1 percent, from about 1 to about 2 percent) by weight of the total composition is believed adequately to provide therapeutic value for combating infection, such as bacterial infection caused by Gram-positive, Gram-negative bacteria or both.

In one embodiment, a composition of the present invention is in a form of a suspension or dispersion. In another embodiment, the suspension or dispersion is based on an aqueous solution. For example, a composition of the present invention can comprise micrometer- or nanometer-sized particles of the active ingredient suspended or dispersed in sterile saline solution. In another embodiment, the suspension or dispersion is based on a hydrophobic medium. For example, the micrometer- or nanometer-sized (such as in the range from about 0.1 to about 10 μm) particles of the active ingredient (or a salt or ester thereof) can be suspended in a hydrophobic solvent e.g., silicone oil, mineral oil, or any other suitable nonaqueous medium for delivery to the eye. In still another embodiment, the micrometer- or nanometer-sized particles of the active ingredient (or a salt or ester thereof) can be coated with a physiologically acceptable surfactant (non-limiting examples are disclosed below), then the coated particles are dispersed in a liquid medium. The coating can keep the particles in a suspension. Such a liquid medium can be selected to produce a sustained-release suspension. For example, the liquid medium can be one that is sparingly soluble in the ocular environment into which the suspension is administered. In still another embodiment, the active ingredient (or a salt or ester thereof) is suspended or dispersed in a hydrophobic medium, such as an oil. In still another embodiment, such a medium comprises an emulsion of a hydrophobic material and water. In still another embodiment, the insoluble active ingredient (or a salt or ester thereof) disclosed herein can be dosed by any normal drug delivery vehicle including but not limited to suspension in a liposome composition (both within and outside the liposome wall or strictly outside the liposome core), in the continuous phase of an emulsion or microemulsion, in the oil phase of the emulsion, or in a micellar solution using either charged or uncharged surfactants. A micellar solution wherein the surfactant is both the micelle forming agent and the anion of the active ingredient (or a salt or ester thereof) disclosed herein would be preferable.

In another aspect, a composition of the present invention can further comprise a non-ionic surfactant, such as polysorbates (such as polysorbate 80 (polyoxyethylene sorbitan monooleate), polysorbate 60 (polyoxyethylene sorbitan monostearate), polysorbate 20 (polyoxyethylene sorbitan monolaurate), commonly known by their trade names of Tween® 80, Tween® 60, Tween® 20), poloxamers (synthetic block polymers of ethylene oxide and propylene oxide, such as those commonly known by their trade names of Pluronic®; e.g., Pluronic® F127 or Pluronic® F108)), or poloxamines (synthetic block polymers of ethylene oxide and propylene oxide attached to ethylene diamine, such as those commonly known by their trade names of Tetronic®; e.g., Tetronic® 1508 or Tetronic® 908, etc., other nonionic surfactants such as Brij®, Myrj®, and long chain fatty alcohols (i.e., oleyl alcohol, stearyl alcohol, myristyl alcohol, docosohexanoyl alcohol, etc.) with carbon chains having about 12 or more carbon atoms (e.g., such as from about 12 to about 24 carbon atoms). Such compounds are delineated in Martindale, $34^{th}$ ed., pp. 1411-1416 (Martindale, "The Complete Drug Reference," S. C. Sweetman (Ed.), Pharmaceutical Press, London, 2005) and in Remington, "The Science and Practice of Pharmacy," $21^{st}$ Ed., p. 291 and the contents of chapter 22, Lippincott Williams & Wilkins, New York, 2006). The concentration of a non-ionic surfactant, when present, in a composition of the present invention can be in the range from about 0.001 to about 5 weight percent (or alternatively, from about 0.01 to about 4, or from about 0.01 to about 2, or from about 0.01 to about 1, or from about 0.01 to about 0.5 weight percent). Any of these surfactants also can be used to coat micrometer- or nanometer-sized particles, as disclosed above.

In addition, a composition of the present invention can include additives such as buffers, diluents, carriers, adjuvants, or other excipients. Any pharmacologically acceptable buffer suitable for application to the eye may be used. Other agents may be employed in the composition for a variety of purposes. For example, buffering agents, preservatives, co-solvents, oils, humectants, emollients, stabilizers, or antioxidants may be employed.

Water-soluble preservatives which may be employed include sodium bisulfite, sodium bisulfate, sodium thiosulfate, benzalkonium chloride, chlorobutanol, thimerosal, ethyl alcohol, methylparaben, polyvinyl alcohol, benzyl alcohol, phenylethyl alcohol, peroxide (such as hydrogen peroxide, urea hydrogen peroxide, or a source that generate a peroxide compound such as perborate), biguanide compounds, and quaternium compounds (such as polyquat-1, polyquat-10, etc.). These agents may be present in individual amounts of from about 0.001 to about 5 percent by weight (preferably, about 0.01 to about 2 percent by weight).

Suitable water-soluble buffering agents that may be employed are sodium carbonate, sodium borate, sodium phosphate, sodium acetate, sodium bicarbonate, etc., as approved by the United States Food and Drug Administration ("US FDA") for the desired route of administration. These agents may be present in amounts sufficient to maintain a pH of the system of between about 5 and about 8. As such, the buffering agent may be as much as about 5 percent on a weight to weight basis of the total composition. Electrolytes such as, but not limited to, sodium chloride and potassium chloride may also be included in the composition. Physiologically acceptable buffers include, but are not limited to, a phosphate buffer or a Tris-HCl buffer (comprising tris(hydroxymethyl)aminomethane and HCl). For example, a Tris-HCl buffer having pH of 7.4 comprises 3 g/l of tris(hydroxymethyl)aminomethane and 0.76 g/l of HCl. In yet another aspect, the buffer is 10× phosphate buffer saline ("PBS") or 5×PBS solution.

Other buffers also may be found suitable or desirable in some circumstances, such as buffers based on HEPES (N-{2-hydroxyethyl}piperazine-N'-{2-ethanesulfonic acid}) having $pK_a$ of 7.5 at 25° C. and pH in the range of about 6.8-8.2; BES (N,N-bis{2-hydroxyethyl}2-aminoethanesulfonic acid) having $pK_a$ of 7.1 at 25° C. and pH in the range of about 6.4-7.8; MOPS (3-{N-morpholino}propanesulfonic acid) having $pK_a$ of 7.2 at 25° C. and pH in the range of about 6.5-7.9; TES (N-tris{hydroxymethyl}-methyl-2-aminoethanesulfonic acid) having $pK_a$ of 7.4 at 25° C. and pH in the range of about 6.8-8.2; MOBS (4-{N-morpholino}butanesulfonic acid) having $pK_a$ of 7.6 at 25° C. and pH in the range of about 6.9-8.3; DIPSO (3-(N,N-bis{2-hydroxyethyl}amino)-2-hydroxypropane)) having $pK_a$ of 7.52 at 25° C. and pH in the range of about 7-8.2; TAPSO (2-hydroxy-3{tris(hydroxymethyl)methylamino}-1-propanesulfonic acid)) having $pK_a$ of 7.61 at 25° C. and pH in the range of about 7-8.2; TAPS ({(2-hydroxy-1,1-bis(hydroxymethyl)ethyl)amino}-1-propanesulfonic acid)) having $pK_a$ of 8.4 at 25° C. and pH in the range of about 7.7-9.1; TABS (N-tris(hydroxymethyl)methyl-4-aminobutanesulfonic acid) having $pK_a$ of 8.9 at 25° C. and pH in the range of about 8.2-9.6; AMPSO (N-(1,1-dimethyl-2-hydroxyethyl)-3-amino-2-hydroxypropanesulfonic acid)) having $pK_a$ of 9.0 at 25° C. and pH in the range of about 8.3-9.7; CHES (2-cyclohexylamino)ethanesulfonic acid) having $pK_a$ of 9.5 at 25° C. and pH in the range of about 8.6-10.0; CAPSO (3-(cyclohexylamino)-2-hydroxy-1-propanesulfonic acid) having $pK_a$ of 9.6 at 25° C. and pH in the range of about 8.9-10.3; or CAPS (3-(cyclohexylamino)-1-propane sulfonic acid) having $pK_a$ of 10.4 at 25° C. and pH in the range of about 9.7-11.1.

In one aspect, the composition has a pH that is suitable for administration into a subject; e.g., to render the composition non-irritating. For example, for topical ophthalmic administration, a desired pH is in the range from about 5 to about 8 (or alternatively from about 6 to about 7, or from about 6.4 to about 6.8).

In one aspect, the composition has a pH of about 7. Alternatively, the composition has a pH in a range from about 7 to about 7.5.

In another aspect, the composition has a pH of about 7.4.

In yet another aspect, a composition also can comprise a viscosity-modifying compound designed to facilitate the administration of the composition into the subject or to promote the bioavailability in the subject. In still another aspect, the viscosity-modifying compound may be chosen so that the composition is not readily dispersed after being administered into an ocular environment (such as the ocular surface, conjunctiva, or vitreous). Such compounds may enhance the viscosity of the composition, and include, but are not limited to: monomeric polyols, such as, glycerol, propylene glycol, ethylene glycol; polymeric polyols, such as, polyethylene glycol; various polymers of the cellulose family, such as hydroxypropylmethyl cellulose ("HPMC"), carboxymethyl cellulose ("CMC") sodium, hydroxypropyl cellulose ("HPC"); polysaccharides, such as hyaluronic acid and its salts, chondroitin sulfate and its salts, dextrans, such as, dextran 70; water soluble proteins, such as gelatin; vinyl polymers, such as, polyvinyl alcohol, polyvinylpyrrolidone, povidone; carbomers, such as carbomer 934P, carbomer 941, carbomer 940, or carbomer 974P; and acrylic acid polymers. In general, a desired viscosity can be in the range from about 1 to about 400 centipoises ("cp" or mPa·s).

In another aspect, the present invention provides a method for producing a composition comprising besifloxacin (or a salt or ester thereof), the method comprising: (a) providing said besifloxacin (or a salt or ester thereof); and (b) dispersing an amount of said besifloxacin (or a salt or ester thereof) in a sufficient amount of said medium to produce said composition to achieve a predetermined concentration of said besifloxacin (or a salt or ester thereof) in said medium. Alternatively, a portion of besifloxacin (or a salt or ester thereof) remains in a solid phase for a period longer than 2 days, or 1 week, or 1 month, or 2 months, or 3 months, or 4 months, or 5 months, or 6 months, or 1 year, or 2 years after said besifloxacin (or a salt or ester thereof) has been in contact with said medium. In one embodiment, the method can optionally include a step of reducing the size of besifloxacin (or a salt or ester thereof) before dispersing such besifloxacin (or a salt or ester thereof) in the medium.

In still another aspect, the present invention provides a method for producing a molecular crystal of besifloxacin. The method comprises: (a) solubilizing a desired amount of a soluble salt of besifloxacin in a solvent (such as water) to form a solution; (b) adjusting the pH of the solution to a value in the range from about 6.2 to about 6.8; and (c) allowing a time sufficient to form the molecular crystal of besifloxacin. The method can further comprise recovering the molecular crystal of besifloxacin with or without further drying the molecular crystal. The method can further comprise subjecting the recovered molecular crystal to a step of size reduction to nanometer- or micrometer-sized particles.

Some compositions of the present invention are disclosed in the examples below. It should be understood that the proportions of the listed ingredients may be adjusted for specific circumstances.

Example 1

TABLE 5

| Ingredient | Amount |
| --- | --- |
| Carbopol 934P NF | 1 g |
| Propylene glycol | 5 g |
| EDTA | 0.1 mg |
| besifloxacin micro particles | 0.6 g |
| Purified water | q.s. to 100 g |

An appropriate proportion of EDTA (e.g., shown in Table 5) is added to purified water in a stainless steel jacketed vessel that is equipped with a stirring mechanism. An appropriate amount of carbopol 934P NF is added, over a period of five to ten minutes to form a substantially uniform dispersion. Propylene glycol is added to the resulting mixture while mixing for three to ten minutes. Then, an appropriate amount to besifloxacin, which may be previously micronized, is added to the contents of the vessel over a period of three to five minutes while mixing continues until the compound is substantially dispersed. The pH of the mixture is adjusted to 6.4-6.7 using 1 N NaOH. The final composition is sterilized, using, for example, heat or radiation and then packaged in appropriate containers.

Example 2

A procedure similar to that disclosed in Example 1 is used to produce the composition of the present invention having the ingredients listed in Table 14.

TABLE 6

| Ingredient | Amount (% by weight, except where "ppm" is indicated) |
| --- | --- |
| Povidone | 1.5 |
| HAP (30%) | 0.05 |
| Glycerin | 3 |
| Propylene glycol | 3 |
| besifloxacin microparticles | 0.7 |
| Alexidine 2HCl | 1-2 ppm |
| Purified water | q.s. to 100 |

Note: "HAP" denotes hydroxyalkyl phosphonates, such as those known under the trade name Dequest®. HAPs can be used as chelating agents and have been shown to inhibit bacterial and fungal cell replication.

Example 3

A procedure similar to that disclosed in Example 1 is used to produce the composition of the present invention having the ingredients listed in Table 7.

TABLE 7

| Ingredient | Amount (% by weight, except where "ppm" is indicated) |
| --- | --- |
| Glycerin | 3 |
| Propylene glycol | 3 |
| Besifloxacin microparticles | 0.4 |
| Polyquat-1 | 1-10 ppm |
| Sunflower oil | q.s. to 100 |

Example 4

A modification of the procedure disclosed in Example 1 is used to produce the composition of the present invention having the ingredients listed in Table 8.

An appropriate proportion of polysorbate 80 (e.g., shown in FIG. 26) is added to approximately 20 percent of the desired final volume of purified water in a stainless steel jacketed vessel that is equipped with a stirring mechanism. Glycerin and propylene glycol are then added to the mixture while mixing continues for five more minutes. To a sterilized second vessel, heated to about 80° C. and equipped with a stirring mechanism, containing approximately 70 percent of the desired final volume of purified water, an appropriate amount of CMC-MV is added over a period of three to five minutes while mixing continues until the CMC forms a substantially uniform solution. The contents of the second vessel are cooled to about room temperature and then the contents of the first vessel are transferred into the second vessel. The remaining of the desired volume of purified water is added to the second vessel. Then, an appropriate amounts of besifloxacin and a second anti-infective drug (such as ciprofloxacin) are added to the contents of the second vessel over a period of three to five minutes while mixing continues until the drugs are substantially uniformly dispersed. The pH of the mixture is adjusted to 6.5-6.7 using 1 N NaOH. The final composition is sterilized, using, for example, heat or radiation, and packaged in appropriate containers.

TABLE 8

| Ingredient | Amount (% by weight, except where "ppm" is indicated) |
| --- | --- |
| Carboxymethyl cellulose, medium viscosity ("CMC-MV") | 0.5 |
| Glycerin | 3 |
| Propylene glycol | 3 |
| Besifloxacin microparticles | 0.6 |
| Cirpofloxacin microparticles | 0.2 |
| Polysorbate 80 ® (a surfactant) | 0.25 |
| Stabilized oxychloro complex | 20-50 ppm |
| Purified water | q.s. to 100 |

Example 5

A procedure similar to that of Example 1 is used to produce a composition comprising the ingredients listed in Table 9.

TABLE 9

| Ingredient | Amount (% by weight, except where "ppm" is indicated) |
| --- | --- |
| Glycerin | 3 |
| Propylene glycol | 3 |
| Besifloxacin microparticles | 0.5 |
| Tween ® 80 | 0.25 |
| Alexidine | 1-2 ppm |
| Corn oil | q.s. to 100 |

Example 6

A procedure similar to that of Example 4 is used to produce a composition comprising the ingredients listed in Table 10.

TABLE 10

| Ingredient | Amount (% by weight, except where "ppm" is indicated) |
| --- | --- |
| CMC (MV) | 0.5 |
| Glycerin | 3 |
| Propylene glycol | 3 |
| Besifloxacin microparticles | 0.75 |
| Moxifloxacin microparticles | 0.25 |
| Tyloxapol (a surfactant) | 0.25 |
| Alexidine 2HCl | 1-2 ppm |
| Purified water | q.s. to 100 |

Example 7

A procedure similar to that of Example 1 is used to produce a composition comprising the ingredients listed in Table 11.

TABLE 11

| Ingredient | Amount (% by weight, except where "ppm" is indicated) |
| --- | --- |
| HPMC | 0.5 |
| Glycerin | 3 |
| Propylene glycol | 3 |
| Besifloxacin microparticles | 0.5 |
| Gatifloxacin microparticles | 0.2 |
| Azithromycin microparticles | 0.2 |
| Tyloxapol (a surfactant) | 0.25 |
| Benzakonium chloride | 100 ppm |
| Purified water | q.s. to 100 |

Alternatively, purified water may be substituted with an oil, such as fish-liver oil, peanut oil, sesame oil, coconut oil, sunflower oil, corn oil, or olive oil to produce an oil-based composition comprising besifloxacin molecular crystal.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°.

2. A molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by a differential scanning calorimetry ("DSC") melting peak at 288° C.

3. A molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by $^{13}$C NMR spectrum having peaks at 23.3, 27.7, 41.1, 54.5, 116.6, and 153.5 ppm.

4. A molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by pKa values of 5.65 and 9.91.

5. A molecular crystal form of (R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid characterized by an X-ray powder diffraction ("XRPD") spectrum that comprises peaks at 2θ angles of 10.6, 15, 19.7, 21.1, and 22°±0.2°; a DSC melting peak at 288° C.; a $^{13}$C NMR spectrum having peaks at 23.3, 27.7, 41.1, 54.5, 116.6, and 153.5 ppm; and by pKa values of 5.65 and 9.91.

6. A method of making a molecular crystal of besifloxacin ((R)-(+)-7-(3-amino-2,3,4,5,6,7-hexahydro-1H-azepin-1-yl)-1-cyclopropyl-8-chloro-6-fluoro-1,4-dihydro-4-oxoquinoline-3-carboxylic acid), comprising: (a) solubilizing a desired amount of a soluble salt of besifloxacin in a solvent (such as water) to form a solution; (b) adjusting the pH of the solution to a value in the range from about 6.2 to about 6.8; and (c) allowing a time sufficient to form the molecular crystal of besifloxacin.

7. The method of claim 6, further comprising recovering the molecular crystal of besifloxacin.

8. The method of claim 7, further comprising subjecting the recovered molecular crystal to a step of size reduction to nanometer- or micrometer-sized particles.

* * * * *